United States Patent
Tolborg et al.

(10) Patent No.: US 9,180,169 B2
(45) Date of Patent: Nov. 10, 2015

(54) GLUCAGON ANALOGUES

(71) Applicants:Zealand Pharma A/S, Glostrup (DK); Boehringer Ingelheim International GmbH, Ingelheim am Rhein (DE)

(72) Inventors: Jakob Lind Tolborg, Herlev (DK); Keld Fosgerau, Vanløse (DK); Pia Nørregaard, Lyngby (DK); Rasmus Just, Copenhagen N (DK); Ditte Riber, Brønshøj (DK); Dieter Wolfgang Hamprecht, Ingelheim am Rhein (DE); Robert Augustin, Ingelheim am Rhein (DE); Leo Thomas, Ingelheim am Rhein (DE); Wolfgang Rist, Ingelheim am Rhein (DE)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 14/029,529

(22) Filed: Sep. 17, 2013

(65) Prior Publication Data

US 2014/0080757 A1    Mar. 20, 2014

Related U.S. Application Data

(60) Provisional application No. 61/701,952, filed on Sep. 17, 2012, provisional application No. 61/784,294, filed on Mar. 14, 2013.

(30) Foreign Application Priority Data

Sep. 17, 2012  (EP) .................................... 12184744

(51) Int. Cl.
    *A61K 45/06*  (2006.01)
    *A61K 38/26*  (2006.01)
    *C07K 14/605* (2006.01)

(52) U.S. Cl.
    CPC ............... *A61K 38/26* (2013.01); *A61K 45/06* (2013.01); *C07K 14/605* (2013.01)

(58) Field of Classification Search
    CPC ....... A61K 38/26; A61K 45/06; C07K 14/605
    See application file for complete search history.

(56) References Cited

U.S. PATENT DOCUMENTS

| | | | |
|---|---|---|---|
| 7,994,122 B2 | 8/2011 | Riber et al. | |
| 8,642,540 B2 | 2/2014 | Meier et al. | |
| 8,642,541 B2 | 2/2014 | Meier et al. | |
| 8,680,049 B2 | 3/2014 | Meier et al. | |
| 8,685,919 B2 | 4/2014 | Meier et al. | |
| 2005/0070469 A1 | 3/2005 | Bloom et al. | |
| 2010/0099601 A1 | 4/2010 | Weiss | |
| 2010/0190701 A1 | 7/2010 | Day et al. | |
| 2011/0286981 A1 | 11/2011 | Meier et al. | |
| 2011/0286982 A1 | 11/2011 | Meier et al. | |
| 2011/0293586 A1 | 12/2011 | Meier et al. | |
| 2011/0293587 A1 | 12/2011 | Meier et al. | |
| 2012/0178670 A1 | 7/2012 | Riber et al. | |
| 2013/0157929 A1 | 6/2013 | Riber et al. | |
| 2013/0157935 A1 | 6/2013 | Meier et al. | |
| 2013/0157953 A1 | 6/2013 | Petersen et al. | |
| 2013/0316941 A1 | 11/2013 | Hamprecht et al. | |
| 2014/0011733 A1 | 1/2014 | Fosgerau et al. | |
| 2014/0080757 A1 | 3/2014 | Tolborg et al. | |
| 2014/0127174 A1 | 5/2014 | Meier et al. | |
| 2014/0127175 A1 | 5/2014 | Meier et al. | |
| 2015/0080295 A1 | 3/2015 | Meier et al. | |
| 2015/0111817 A1 | 4/2015 | Riber et al. | |
| 2015/0111826 A1 | 4/2015 | Riber et al. | |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 2025684 A1 | 2/2009 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |

(Continued)

OTHER PUBLICATIONS

Abbrecht et al., "Erythrocyte life-span in mice acclimatized to different degrees of hypoxia," J Appl Physiol. 32(4):443-445 (1972).
Adelhorst et al., "Structure-activity studies of glucagon-like peptide-1," J Biol Chem. 269(9):6275-6278 (1994).
Altschul et al., "Local Alignment Statistics," Methods Enzymol. 266:460-480 (1996).
Authier et al., "Endosomal proteolysis of glucagon at neutral pH generates the bioactive degradation product miniglucagon-(19-29)," Endocrinology. 144(12):5353-5364 (2003).
Blache et al., "Endopeptidase from rat liver membranes, which generates miniglucagon from glucagon," J Biol Chem. 268(29):21748-21753 (1993).

(Continued)

*Primary Examiner* — Thomas S Heard
(74) *Attorney, Agent, or Firm* — Clark & Elbing LLP; Kristina Biecker-Brady

(57) ABSTRACT

The invention provides materials and methods for the treatment of obesity and excess weight, diabetes, and other associated metabolic disorders. In particular, the invention provides novel glucagon analog peptides effective in such methods. The peptides may mediate their effect by having increased selectivity for the GLP-1 receptor as compared to human glucagon.

15 Claims, No Drawings

(56) References Cited

FOREIGN PATENT DOCUMENTS

| | | |
|---|---|---|
| WO | WO-2004/096854 A2 | 11/2004 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/100535 A2 | 9/2007 |
| WO | WO-2008/010101 A2 | 1/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/067636 A2 | 5/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/014946 A2 | 2/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2011/006497 A1 | 1/2011 |
| WO | WO-2011/088837 A1 | 7/2011 |
| WO | WO-2011/160630 A2 | 12/2011 |
| WO | WO-2011/160633 A1 | 12/2011 |
| WO | WO-2012/098462 A1 | 7/2012 |
| WO | WO-2013/092703 A2 | 6/2013 |
| WO | WO-2014/041195 A1 | 3/2014 |

OTHER PUBLICATIONS

Cavanaugh et al., "Isolation and structural characterization of proglucagon-derived peptides, pancreatic polypeptide, and somatostatin from the urodele *Amphiuma tridactylum*," Gen Compar Endocrin. 101:12-20 (1996).

Chan et al., "Suppression of weight gain by glucagon in obese Zucker rats," Exp Mol Path. 40:320-327 (1984).

Cohen et al., "Oxyntomodulin suppresses appetite and reduces food intake in humans," J Clin Endocrinol Metab. 88(10):4696-4701 (2003).

Dakin et al., "Oxyntomodulin inhibits food intake in the rat," Endocrinology. 142:4244-4250 (2001).

Dakin et al., "Peripheral oxyntomodulin reduces food intake and body weight gain in rats," Endocrinology. 145(6):2687-2695 (2004).

Day et al., "A new glucagon and GLP-1 co-agonist eliminates obesity in rodents," Nat Chem Biol. 5(10):749-757 (2009).

Delgado et al., "The uses and properties of PEG-linked proteins," Crit Rev Ther Drug Carrier Syst. 9(3,4):249-304 (1992).

Druce et al., "Investigation of structure-activity relationships of Oxyntomodulin (Oxm) using Oxm analogs," Endocrinology. 150:1712-1721 (2009).

England et al., "Glucagon carboxyl-terminal derivatives: Preparation, purification and characterization," Biochemistry. 21:940-950 (1982).

Francis et al., "PEGylation of cytokines and other therapeutic proteins and peptides: the importance of biological optimisation of coupling techniques," Int J Hematol. 68:1-18 (1998).

Frandsen et al., "Glucagon: structure-function relationships investigated by sequence deletions," Hoppe Seylers Z Physiol Chem. 362:665-677 (1981).

Gelfanov et al., Discovery and structural optimization of high affinity co-agonists at the glucagon and GLP-1 receptors. *Understanding Biology Using Peptides*. Sylvie E. Blondelle, 763-764 (2005).

Göke et al.,"Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).

Gombotz et al. "Biodegradable polymers for protein and peptide drug delivery," Bioconjugate Chem. 6:332-351 (1995).

Hjorth et al., "Glucagon and glucagon-like peptide 1: Selective receptor recognition via distinct peptide epitopes," J Biol Chem. 269(48):30121-30124 (1994).

Hruby et al., "The design and biological activities of glucagon agonists and antagonists, and their use in examining the mechanisms of glucose action," Curr Med Chem—Imm, Endoc Metab Agents. 1(3):199-215 (2001).

Hudecz et al., "Synthesis, conformation, biodistribution, and in vitro cytotoxicity of daunomycin-branched polypeptide conjugates," Bioconjugate Chem. 3(1):49-57 (1992).

Joshi et al., "The estimation of glutaminyl deamidation and aspartyl cleavage rates in glucagon," Int J Pharma. 273:213-219 (2004).

Kallenbach et al., "Role of the peptide bond in protein structure and folding," *The amide linkage: selected structural aspects in chemistry, biochemistry, and materials science*. John Wiley & Sons Inc. 599-622 (2000).

Knudsen et al., "Potent derivatives of glucagon-like peptide-1 with pharmacokinetic properties suitable for once daily administration," J Med Chem. 43(9):1664-1669 (2000).

Madsen et al., "Structure-activity and protraction relationship of long-acting glucagon-like peptide-1 derivatives: importance of fatty acid length, polarity, and bulkiness," J Med Chem. 50(54):6126-6132 (2007).

McKee et al., "Receptor binding and adenylate cyclase activities of glucagon analogues modified in the N-terminal region," Biochemistry. 25(7):1650-1656 (1986).

NCBI Blast for Accession No. 721913A. Retrieved on Dec. 15, 2009 (1 page.).

Pan et al, "Design of a long acting peptide functioning as both a glucagon-like peptide-1 receptor agonist and a glucagon receptor antagonist, " J Biol Chem. 281(18):12506-12515 (2006).

Parlevliet et al., "Oxyntomodulin ameliorates glucose intolerance in mice fed a high-fat diet," Am J Physiol Endocrinol Metab. 294:E142-E147 (2008).

Pratesi et al., "Poly-L-aspartic acid as a carrier for doxorubicin: a comparative in vivo study of free and polymer-bound drug," Br J Cancer. 52:841-848 (1985).

Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).

Unson et al., "Glucagon antagonists: contribution to binding and activity of the amino-terminal sequence 1-5, position 12, and the putative alpha-helical segment 19-27," J Biol Chem. 264(2):789-794 (1989).

Unson et al., "Identification of an essential serine residue in glucagon: implication for an active site triad," Proc Natl Acad Sci USA. 91:454-458 (1994).

Unson et al., "Positively charged residues at positions 12, 17, and 18 of glucagon ensure maximum biological potency," J Biol Chem. 273(17):10308-10312 (1998).

Zalipsky, "Functionalized poly(ethylene glycol) for preparation of biologically relevant conjugates," Bioconjugate Chem. 6(2):150-165 (1995).

Zhu et al.,"The role of dipeptidyl peptidase IV in the cleavage of glucagon family peptides: in Vivo metabolism of pituitary Adenylate cyclase activating polypeptide-(1-38)," J Biol Chem. 278:22418-22423 (2003).

International Search Report for International Application No. PCT/IB2012/000134, mailed Jun. 25, 2012 (3 pages).

U.S. Appl. No. 14/516,216, Riber et al.

U.S. Appl. No. 14/517,497, Riber et al.

U.S Appl. No. 14/195,533, Meier et al.

Jaya et al., "Mechanism of hypocholesterolemic action of glucagon." J Biosci. 12(2):111-4 (1987).

Hostrup et al., Modification of Peptides and Proteins. *Delivery Technologies for Biopharmaceuticals: Peptides, Proteins, Nucleic Acids and Vaccines*. Wiley & Sons, 171-91 (2009).

(56) References Cited

OTHER PUBLICATIONS

Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Wermuth, "Glossary of terms used in medicinal chemistry," Pure & Appl Chem. 70(5):1129-43 (1998).
Written Opinion for Singapore Application No. 201209089-0 dated Nov. 8, 2013 (10 pages).
International Search Report for International Application No. PCT/DK2010/000099, mailed Dec. 2, 2010 (2 pages).
International Search Report for PCT/DK2011/000067 mailed Dec. 9, 2011 (4 pages).
International Search Report for PCT/DK2011/000072, mailed Dec. 6, 2011 (3 pages).
International Search Report and Written Opinion for PCT/GB2008/004121 mailed Jun. 30, 2009 (25 pages).
International Search Report for PCT/GB2008/004157 mailed Jun. 4, 2009 (6 pages).
International Search Report and Written Opinion for PCT/GB2008/004130 mailed Mar. 25, 2009 (17 pages).
International Search Report and Written Opinion for PCT/GB2008/004132 mailed Jun. 10, 2009 (16 pages).
Communication from the European Patent Office for European Patent Application No. 08 875 673.9-2405 dated Jul. 4, 2012 (6 pages).
Ali et al., "Cardiomyocyte glucagon receptor signaling modulates outcomes in mice with experimental myocardial infarction," Mol Metab. 4(2):132-143 (2015).
Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
European Search Report from European Patent Application No. 07016032.0, completed Jan. 28, 2008 (8 pages).
Goldstein et al., "Effects of chronic heart failure on the capacity of glucagon to enhance contractility and adenyl cyclase activity of human papillary muscles," Circulation. 44(4):638-648 (1971).
International Preliminary Report on Patentability for PCT/EP2013/069286, completed Jan. 19, 2015 (40 pages).
International Preliminary Report on Patentability for PCT/GB2008/002041, issued Dec. 17, 2009 (7 pages).
International Search Report and Written Opinion for PCT/EP2013/069286, mailed Dec. 18, 2013 (16 pages).
International Search Report for PCT/DK2010/000099, mailed Dec. 2, 2010 (2 pages).
International Search Report for PCT/GB2008/002041, mailed Sep. 9, 2008 (3 pages).
Mehta, "Diabetic cardiomyopathy: insights into pathogenesis, diagnostic challenges, and therapeutic options," Intl J Pharm Sci Res. 3(10):3565-3576 (2012).
Pocai et al., "Glucagon-like peptide 1/glucagon receptor dual agonism reverses obesity in mice," Diabetes. 58(10):2258-66 (2009).
Pocai, "Glucagon signaling in the heart: activation or inhibition?," Mol Metab. 4(2):81-2 (2015).
Protest of U.S. Appl. No. 12/664,534 Pursuant 37 CFR 1.291, mailed Jan. 13, 2010 (14 pages).
Rose et al., "Insulin proteinase liberates from glucagon a fragment known to have enhanced activity against $Ca^{2+} + Mg^{2+}$-dependent ATPase," Biochem J. 256(3):847-51 (1988).
Written Opinion for PCT/DK2011/000072, mailed Dec. 6, 2011 (6 pages).
Written Opinion of the International Searching Authority for PCT/GB2008/002041, mailed Sep. 9, 2008 (6 pages).

SEQUENCE LISTING

<160> NUMBER OF SEQ ID NOS: 46

<210> SEQ ID NO 1
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 1

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Leu Ser
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 2

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Ser Ala
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic construct: Peptide X of Claim 2
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 3

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Arg Ala
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)

```
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 4

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Leu Ser Ala
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 5

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Glu Ser Ala
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 6

His Ser Gln Gly Thr Phe Thr Ser Asp Tyr Ser Arg Tyr Leu Asp Ser
1               5                   10                  15

Xaa Ala Ala Glu Asp Phe Val Glu Trp Leu Leu Arg Ala
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 7

His Ser Gln Gly Thr Phe Thr Ser Asp Tyr Ser Lys Tyr Leu Asp Ser
1               5                   10                  15
```

Xaa Ala Ala Glu Asp Phe Val Glu Trp Leu Leu Arg Ala
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 8

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Ser
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 9

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Arg
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 10

His Ser Gln Gly Thr Phe Thr Ser Asp Tyr Ser Lys Tyr Leu Asp Glu
1               5                   10                  15

Xaa Ala Ala His Glu Phe Val Glu Trp Leu Glu Ser Ala
            20                  25

<210> SEQ ID NO 11
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES

```
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 11

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Leu Ser
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 12

His Ser Gln Gly Thr Phe Thr Ser Asp Tyr Ser Arg Tyr Leu Asp Ser
1               5                   10                  15

Xaa Ala Ala His Asp Phe Val Glu Trp Leu Leu Ser Ala
            20                  25

<210> SEQ ID NO 13
<211> LENGTH: 29
<212> TYPE: PRT
<213> ORGANISM: Artificial Sequence
<220> FEATURE:
<223> OTHER INFORMATION: Synthetic construct: Peptide X of Claim 2
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 13

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Leu Ser Ala
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic construct: Peptide X of Claim 2
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 14

His Xaa Gln Gly Thr Phe Thr Ser Asp Tyr Ser Lys Tyr Leu Asp Glu
1               5                   10                  15
```

```
Xaa Arg Ala Lys Asp Phe Ile Glu Trp Leu Leu Ser Ala
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthetic construct: Peptide X of Claim 3
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 15

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic construct: Peptide X of Claim 6
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 16

His Xaa Gln Gly Thr Phe Thr Ser Asp Tyr Ser Lys Tyr Leu Asp Ser
1               5                   10                  15

Xaa Ala Ala Glu Asp Phe Val Glu Trp Leu Glu Ser Ala
            20                  25

<210> SEQ ID NO 17
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 17

His Xaa His Gly Thr Phe Thr Ser Asp Tyr Ser Lys Tyr Leu Glu Ser
1               5                   10                  15

Xaa Ala Ala Glu Glu Phe Ile Glu Trp Leu Glu Ser Ala
            20                  25
```

```
<210> SEQ ID NO 18
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 18

His Ser His Gly Thr Phe Thr Ser Asp Tyr Ser Lys Tyr Leu Glu Glu
1               5                   10                  15

Xaa Ala Ala His Glu Phe Ile Glu Trp Leu Glu Ser Ala
            20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 19

His Xaa His Gly Thr Phe Thr Ser Asp Tyr Ser Lys Tyr Leu Glu Glu
1               5                   10                  15

Xaa Ala Ala His Glu Phe Val Glu Trp Leu Glu Ser Ala
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 20

His Xaa Gln Gly Thr Phe Thr Ser Asp Tyr Ser Lys Tyr Leu Glu Glu
1               5                   10                  15

Xaa Ala Ala Lys Asp Phe Ile Glu Trp Leu Glu Ser Ala
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
```

-continued

```
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 21

His Xaa Gln Gly Thr Phe Thr Ser Asp Tyr Ser Lys Tyr Leu Glu Ser
1               5                   10                  15

Xaa Ala Ala Glu Asp Phe Ile Glu Trp Leu Glu Ser Ala
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 22

His Ser Gln Gly Thr Phe Thr Ser Asp Tyr Ser Lys Tyr Leu Glu Glu
1               5                   10                  15

Xaa Ala Ala Lys Asp Phe Ile Glu Trp Leu Glu Ser Ala
            20                  25

<210> SEQ ID NO 23
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 23

His Xaa Gln Gly Thr Phe Thr Ser Asp Tyr Ser Lys Tyr Leu Glu Ser
1               5                   10                  15

Xaa Ala Ala His Asp Phe Val Glu Trp Leu Glu Ser Ala
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)
```

```
<400> SEQUENCE: 24

His Xaa Gln Gly Thr Phe Thr Ser Asp Tyr Ser Lys Tyr Leu Glu Ser
1               5                   10                  15

Xaa Ala Ala Glu Asp Phe Val Glu Trp Leu Glu Ser Ala
            20                  25

<210> SEQ ID NO 25
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 25

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 26
<211> LENGTH: 29
<212> TYPE: PRT
<213> ORGANISM: Homo sapiens

<400> SEQUENCE: 26

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 27
<211> LENGTH: 8
<212> TYPE: PRT
<213> ORGANISM: Homo sapiens

<400> SEQUENCE: 27

Lys Arg Asn Arg Asn Asn Ile Ala
1               5

<210> SEQ ID NO 28
<211> LENGTH: 37
<212> TYPE: PRT
<213> ORGANISM: Homo sapiens

<400> SEQUENCE: 28

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 29
<211> LENGTH: 48
```

```
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (29)..(48)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 29

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 30
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 30

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 31
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 31

His Xaa Gln Gly Thr Phe Thr Ser Asp Tyr Ser Lys Tyr Leu Asp Glu
1               5                   10                  15
```

-continued

```
Lys Ala Ala Lys Asp Phe Ile Glu Trp Leu Leu Ser Ala Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa

<210> SEQ ID NO 32
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 32

His Xaa Gln Gly Thr Phe Thr Ser Asp Tyr Ser Lys Tyr Leu Asp Ser
1               5                   10                  15

Lys Ala Ala His Asp Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa

<210> SEQ ID NO 33
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 33

His Ser Gln Gly Thr Phe Thr Ser Asp Tyr Ser Arg Tyr Leu Asp Ser
1               5                   10                  15

Lys Ala Ala Glu Asp Phe Val Glu Trp Leu Leu Arg Ala Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa

<210> SEQ ID NO 34
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
``` represents a sequence of 1-20 amino acid units independently
selected from the group consisting of Ala, Leu, Ser, Thr, Tyr,
Cys, Glu, Lys, Arg, Dbu, Dpr and Orn

<400> SEQUENCE: 34

His Ser Gln Gly Thr Phe Thr Ser Asp Tyr Ser Lys Tyr Leu Asp Ser
1               5                   10                  15

Lys Ala Ala Glu Asp Phe Val Glu Trp Leu Leu Arg Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 35
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (29)..(48)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 35

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 36
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (29)..(48)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 36

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 37
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)

```
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 37

His Ser Gln Gly Thr Phe Thr Ser Asp Tyr Ser Lys Tyr Leu Asp Glu
1               5                   10                  15

Lys Ala Ala His Glu Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 38
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (29)..(48)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 38

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Leu Ser Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 39
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 39

His Ser Gln Gly Thr Phe Thr Ser Asp Tyr Ser Arg Tyr Leu Asp Ser
1               5                   10                  15

Lys Ala Ala His Asp Phe Val Glu Trp Leu Leu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 40
<211> LENGTH: 49
```

```
<212> TYPE: PRT
<213> ORGANISM: Artificial Sequence
<220> FEATURE:
<223> OTHER INFORMATION: Synthetic construct: Peptide X-Z of Claim 3
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 40

His Xaa Gln Gly Thr Phe Thr Ser Asp Tyr Ser Lys Tyr Leu Asp Glu
1               5                   10                  15

Lys Ala Ala Lys Asp Phe Ile Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 41
<211> LENGTH: 49
<212> TYPE: PRT
<213> ORGANISM: Artificial Sequence
<220> FEATURE:
<223> OTHER INFORMATION: Synthetic construct: Peptide X-Z of Claim 6
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 41

His Xaa Gln Gly Thr Phe Thr Ser Asp Tyr Ser Lys Tyr Leu Asp Ser
1               5                   10                  15

Lys Ala Ala Glu Asp Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 42
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn
```

```
<400> SEQUENCE: 42

His Xaa His Gly Thr Phe Thr Ser Asp Tyr Ser Lys Tyr Leu Glu Ser
1               5                   10                  15

Lys Ala Ala Glu Glu Phe Ile Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa

<210> SEQ ID NO 43
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 43

His Ser His Gly Thr Phe Thr Ser Asp Tyr Ser Lys Tyr Leu Glu Glu
1               5                   10                  15

Lys Ala Ala His Glu Phe Ile Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa

<210> SEQ ID NO 44
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 44

His Xaa His Gly Thr Phe Thr Ser Asp Tyr Ser Lys Tyr Leu Glu Glu
1               5                   10                  15

Lys Ala Ala His Glu Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa

<210> SEQ ID NO 45
<211> LENGTH: 477
<212> TYPE: PRT
<213> ORGANISM: Homo sapiens
```

<400> SEQUENCE: 45

```
Met Pro Pro Cys Gln Pro Gln Arg Pro Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
    370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
```

```
                    405                 410                 415
Arg Trp Arg Leu Gly Lys Val Leu Trp Glu Glu Arg Asn Thr Ser Asn
            420                 425                 430

His Arg Ala Ser Ser Pro Gly His Gly Pro Pro Ser Lys Glu Leu
        435                 440                 445

Gln Phe Gly Arg Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475

<210> SEQ ID NO 46
<211> LENGTH: 463
<212> TYPE: PRT
<213> ORGANISM: Homo sapiens

<400> SEQUENCE: 46

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Leu Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
    290                 295                 300
```

```
Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Ser Lys Leu Lys
            325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
        370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
            405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
            435                 440                 445

Ala Gly Ser Ser Met Tyr Thr Ala Thr Cys Gln Ala Ser Cys Ser
450                 455                 460
```

GLUCAGON ANALOGUES

CROSS-REFERENCE TO RELATED APPLICATIONS

This application claims the benefit of U.S. Provisional Application No. 61/701,952, filed on Sep. 17, 2012, European Application No. 12184744.6, filed on Sep. 17, 2012, and U.S. Provisional Application No. 61/784,294, filed on Mar. 14, 2013, which are hereby incorporated by reference.

FIELD OF THE INVENTION

The present invention relates to glucagon analogues and their medical use, for example in the treatment of obesity and excess weight, diabetes, and other metabolic disorders.

BACKGROUND OF THE INVENTION

Pre-proglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon. Oxyntomodulin (OXM) is a 37 amino acid peptide which includes the complete 29 amino acid sequence of glucagon with an octapeptide carboxyterminal extension (amino acids 82 to 89 of pre-proglucagon, and termed "intervening peptide 1" or IP-1. The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia.

GLP-1 decreases elevated blood glucose levels by improving glucose-stimulated insulin secretion and promotes weight loss chiefly through decreasing food intake.

OXM is released into the blood in response to food ingestion and in proportion to meal calorie content. OXM has been shown to suppress appetite and inhibit food intake in humans (Cohen et al, Journal of Endocrinology and Metabolism, 88, 4696-4701, 2003; WO 2003/022304). In addition to those anorectic effects, which are similar to those of GLP-1, OXM must also affect body weight by another mechanism, since rats treated with oxyntomodulin show less body weight gain than pair-fed rats (Bloom, Endocrinology 2004, 145, 2687). Treatment of obese rodents with OXM also improves their glucose tolerance (Parlevliet et al, Am J Physiol Endocrinol Metab, 294, E142-7, 2008) and suppresses body weight gain (WO 2003/022304).

OXM activates both the glucagon and the GLP-1 receptors with a two-fold higher potency for the glucagon receptor (SEQ ID NO:45) over the GLP-1 receptor (SEQ ID NO:46), but is less potent than native glucagon and GLP-1 on their respective receptors. Human glucagon is also capable of activating both receptors, though with a strong preference for the glucagon receptor over the GLP-1 receptor. GLP-1 on the other hand is not capable of activating glucagon receptors. The mechanism of action of oxyntomodulin is not well understood. In particular, it is not known whether some of the extrahepatic effects of the hormone are mediated through the GLP-1 and glucagon receptors, or through one or more unidentified receptors.

Other peptides have been shown to bind and activate both the glucagon and the GLP-1 receptor (Hjort et al, Journal of Biological Chemistry, 269, 30121-30124, 1994) and to suppress body weight gain and reduce food intake (see, for example, WO 2006/134340, WO 2007/100535, WO 2008/10101, WO 2008/152403, WO 2009/155257, WO 2009/155258, WO2010/070252, WO2010/070253, WO2010/070255, WO2010/070251, WO2011/006497, WO2011/160630, WO2011/160633).

Obesity is a globally increasing health problem is associated with various diseases, particularly cardiovascular disease (CVD), type 2 diabetes, obstructive sleep apnea, certain types of cancer, and osteoarthritis. As a result, obesity has been found to reduce life expectancy. According to 2005 projections by the World Health Organization there are 400 million adults (age >15) classified as obese worldwide. In the US, obesity is now believed to be the second-leading cause of preventable death after smoking.

The rise in obesity drives an increase in diabetes, and approximately 90% of people with type 2 diabetes may be classified as obese. There are 246 million people worldwide with diabetes, and by 2025 it is estimated that 380 million will have diabetes. Many have additional cardiovascular risk factors, including high/aberrant LDL and triglycerides and low HDL.

SUMMARY OF THE INVENTION

In a first aspect, the invention provides a compound having the formula:

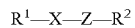

wherein
$R^1$ is H, $C_{1-4}$ alkyl, acetyl, formyl, benzoyl or trifluoroacetyl;
$R^2$ is OH or $NH_2$;
X is a peptide which has the formula:

```
                                         (SEQ ID NO: 1)
H-Aib-QGTFTSDYSKYLDSKAAHDFVEWLLS (SEQ ID NO: 2)
HSQGTFTSDYSKYLDSKAAHDFVEWLLSA (SEQ ID NO: 4)
H-Aib-QGTFTSDYSKYLDEKAAKDFIEWLLSA (SEQ ID NO: 5)
H-Aib-QGTFTSDYSKYLDSKAAHDFVEWLESA (SEQ ID NO: 6)
HSQGTFTSDYSRYLDSKAAEDFVEWLLRA (SEQ ID NO: 7)
HSQGTFTSDYSKYLDSKAAEDFVEWLLRA (SEQ ID NO: 8)
HSQGTFTSDYSKYLDSKAAHDFVEWLLS (SEQ ID NO: 9)
HSQGTFTSDYSKYLDSKAAHDFVEWLLR (SEQ ID NO: 10)
HSQGTFTSDYSKYLDEKAAHEFVEWLESA
```

-continued

```
                                                (SEQ ID NO: 11)
H-Aib-QGTFTSDYSKYLDEKRAKDFIEWLLS (SEQ ID NO: 12)
HSQGTFTSDYSRYLDSKAAHDFVEWLLSA (SEQ ID NO: 17)
H-Aib-HGTFTSDYSKYLESKAAEEFIEWLESA (SEQ ID NO: 18)
HSHGTFTSDYSKYLEEKAAHEFIEWLESA (SEQ ID NO: 19)
H-Aib-HGTFTSDYSKYLEEKAAHEFVEWLESA
``` and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt or solvate thereof (SEQ ID NOs:29-39, 42-44).

In a second aspect, the invention provides a compound of the formula:

$R^1$—X—OH wherein
$R^1$ is H, $C_{1-4}$ alkyl, acetyl, formyl, benzoyl or trifluoroacetyl;
and X is a peptide of SEQ ID NO: 3, 13 or 14:

```
                                                (SEQ ID NO: 3)
HSQGTFTSDYSKYLDSKAAHDFVEWLLRA (SEQ ID NO: 13)
H-Aib-QGTFTSDYSKYLDSKAAHDFVEWLLSA (SEQ ID NO: 14)
H-Aib-QGTFTSDYSKYLDEKRAKDFIEWLLSA
``` or a pharmaceutically acceptable salt or solvate thereof.

In a third aspect, the invention provides a compound having the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 15:

```
                                                (SEQ ID NO: 15)
H-Aib-QGTFTSDYSKYLDEKAAKDFIEWLESA
``` or which differs from SEQ ID NO: 15 at up to three of the following positions whereby, if different from SEQ ID NO: 15:
the residue at position 2 is selected from Ser and D-Ser
the residue at position 3 is selected from His and Hse
the residue at position 12 is Arg
the residue at position 15 is Glu
the residue at position 16 is Ser
the residue at position 18 is Arg
the residue at position 20 is selected from His and Glu
the residue at position 21 is Glu
the residue at position 23 is Val
the residue at position 28 is selected from Arg and Glu
the residue at position 29 is absent;
and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt or solvate thereof (SEQ ID NO:40).

In certain embodiments, the residue at position 20 is not variable and is His.

The compound may have the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 15:

```
                                                (SEQ ID NO: 15)
H-Aib-QGTFTSDYSKYLDEKAAKDFIEWLESA
``` or which differs from SEQ ID NO: 15 at one or both of the following positions whereby, if different from SEQ ID NO: 15:
the residue at position 21 is Glu
the residue at position 23 is Val
and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt or solvate thereof.

In a fourth aspect, the invention provides a compound having the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 16:

```
                                                (SEQ ID NO: 16)
H-Aib-QGTFTSDYSKYLDSKAAEDFVEWLESA
``` or which differs from SEQ ID NO: 16 at up to three of the following positions whereby, if different from SEQ ID NO: 16:
the residue at position 2 is selected from Ser and D-Ser
the residue at position 3 is selected from His and Hse
the residue at position 12 is Arg
the residue at position 15 is Glu
the residue at position 16 is Glu
the residue at position 18 is Arg
the residue at position 20 is selected from Lys and His
the residue at position 21 is Glu
the residue at position 23 is Ile
the residue at position 28 is selected from Arg and Glu
the residue at position 29 is absent
and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt or solvate thereof (SEQ ID NO:41).

The compound may have the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 16:

```
                                                (SEQ ID NO: 16)
H-Aib-QGTFTSDYSKYLDSKAAEDFVEWLESA
``` or which differs from SEQ ID NO: 16 at one or both of the following positions whereby, if different from SEQ ID NO: 16:
the residue at position 21 is Glu
the residue at position 23 is Ile
and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt or solvate thereof.

A compound of the third or fourth aspects of the invention may comprise a peptide X having the sequence:

```
                                         (SEQ ID NO: 15)
H-Aib-QGTFTSDYSKYLDEKAAKDFIEWLESA (SEQ ID NO: 16)
H-Aib-QGTFTSDYSKYLDSKAAEDFVEWLESA (SEQ ID NO: 20)
H-Aib-QGTFTSDYSKYLEEKAAKDFIEWLESA (SEQ ID NO: 21)
H-Aib-QGTFTSDYSKYLESKAAEDFIEWLESA (SEQ ID NO: 22)
HSQGTFTSDYSKYLEEKAAKDFIEWLESA (SEQ ID NO: 23)
H-Aib-QGTFTSDYSKYLESKAAHDFVEWLESA (SEQ ID NO: 24)
H-Aib-QGTFTSDYSKYLESKAAEDFVEWLESA
or (SEQ ID NO: 25)
H-DSer-QGTFTSDYSKYLDEKAAKDFIEWLESA.
```

An any aspect, the compound of the invention may have the formula:

```
                                         (SEQ ID NO: 1)
H-H-Aib-QGTFTSDYSKYLDSKAAHDFVEWLLS-OH (SEQ ID NO: 2)
H-HSQGTFTSDYSKYLDSKAAHDFVEWLLSA-OH (SEQ ID NO: 4)
H-H-Aib-QGTFTSDYSKYLDEKAAKDFIEWLLSA-NH$_2$ (SEQ ID NO: 5)
H-H-Aib-QGTFTSDYSKYLDSKAAHDFVEWLESA-NH$_2$ (SEQ ID NO: 6)
H-HSQGTFTSDYSRYLDSKAAEDFVEWLLRA-NH$_2$ (SEQ ID NO: 7)
H-HSQGTFTSDYSKYLDSKAAEDFVEWLLRA-NH$_2$ (SEQ ID NO: 8)
H-HSQGTFTSDYSKYLDSKAAHDFVEWLLS-NH$_2$ (SEQ ID NO: 9)
H-HSQGTFTSDYSKYLDSKAAHDFVEWLLR-OH (SEQ ID NO: 10)
H-HSQGTFTSDYSKYLDEKAAHEFVEWLESA-NH$_2$ (SEQ ID NO: 11)
H-H-Aib-QGTFTSDYSKYLDEKRAKDFIEWLLS-OH (SEQ ID NO: 12)
H-HSQGTFTSDYSRYLDSKAAHDFVEWLLSA-NH$_2$ (SEQ ID NO: 3)
H-HSQGTFTSDYSKYLDSKAAHDFVEWLLRA-OH (SEQ ID NO: 13)
H-H-Aib-QGTFTSDYSKYLDSKAAHDFVEWLLSA-OH (SEQ ID NO: 14)
H-H-Aib-QGTFTSDYSKYLDEKRAKDFIEWLLSA-OH (SEQ ID NO: 15)
H-H-Aib-QGTFTSDYSKYLDEKAAKDFIEWLESA-NH$_2$ (SEQ ID NO: 16)
H-H-Aib-QGTFTSDYSKYLDSKAAEDFVEWLESA-NH$_2$ (SEQ ID NO: 17)
H-Aib-HGTFTSDYSKYLESKAAEEFIEWLESA-OH (SEQ ID NO: 18)
H-HSHGTFTSDYSKYLEEKAAHEFIEWLESA-OH (SEQ ID NO: 19)
H-H-Aib-HGTFTSDYSKYLEEKAAHEFVEWLESA-NH$_2$ (SEQ ID NO: 20)
H-H-Aib-QGTFTSDYSKYLEEKAAKDFIEWLESA-NH$_2$ (SEQ ID NO: 21)
H-H-Aib-QGTFTSDYSKYLESKAAEDFIEWLESA-NH$_2$ (SEQ ID NO: 22)
H-HSQGTFTSDYSKYLEEKAAKDFIEWLESA-NH$_2$ (SEQ ID NO: 23)
H-H-Aib-QGTFTSDYSKYLESKAAHDFVEWLESA-NH$_2$ (SEQ ID NO: 24)
H-H-Aib-QGTFTSDYSKYLESKAAEDFVEWLESA-NH$_2$ (SEQ ID NO: 25)
H-H-DSer-QGTFTSDYSKYLDEKAAKDFIEWLESA-NH$_2$
``` or may be a pharmaceutically acceptable salt or solvate thereof.

For the avoidance of doubt, in compounds of the third and fourth aspects of the invention, those positions which are not expressly stated to permit variability are intended to be fixed and thus only include the stated residue at those positions.

In all aspects of the invention, one or more of the amino acid side chains in the peptide X or Z (where present) may be conjugated to a lipophilic substituent.

Preferably, one or more of the amino acid side chains in the peptide X is conjugated to the lipophilic substituent.

A lipophilic substituent may have the formula $Z^1$ wherein $Z^1$ is a lipophilic moiety conjugated (covalently linked) directly to the side chain of the relevant residue of X or Z, or $Z^1Z^2$ where $Z^1$ is a lipophilic moiety, $Z^2$ is a spacer, and $Z^1$ is conjugated to the side chain of the residue of X or Z via $Z^2$.

Additionally or alternatively, one or more of the amino acid side chains in peptide X or Z (where present) is conjugated to a polymeric substituent.

In certain embodiments, the peptide X or X—Z carries only one lipophilic substituent and/or only one polymeric substituent.

Lipophilic and polymeric substituents are described in more detail below.

The lipophilic moiety and/or polymeric substituent may be conjugated to the side chain of any suitable residue. A lysine residue may be particularly suitable, e.g. a lysine residue at position 12 (if present) or 17.

Thus peptide X may have the formula:

```
                                         (SEQ ID NO: 1)
H-Aib-QGTFTSDYSKYLDSK*AAHDFVEWLLS (SEQ ID NO: 2)
HSQGTFTSDYSKYLDSK*AAHDFVEWLLSA (SEQ ID NO: 4)
H-Aib-QGTFTSDYSKYLDEK*AAKDFIEWLLSA (SEQ ID NO: 5)
H-Aib-QGTFTSDYSKYLDSK*AAHDFVEWLESA (SEQ ID NO: 6)
HSQGTFTSDYSRYLDSK*AAEDFVEWLLRA
```

```
                                                  (SEQ ID NO: 7)
HSQGTFTSDYSKYLDSK*AAEDFVEWLLRA (SEQ ID NO: 8)
HSQGTFTSDYSKYLDSK*AAHDFVEWLLS (SEQ ID NO: 9)
HSQGTFTSDYSKYLDSK*AAHDFVEWLLR (SEQ ID NO: 10)
HSQGTFTSDYSKYLDEK*AAHEFVEWLESA (SEQ ID NO: 11)
H-Aib-QGTFTSDYSKYLDEK*RAKDFIEWLLS (SEQ ID NO: 12)
HSQGTFTSDYSRYLDSK*AAHDFVEWLLSA (SEQ ID NO: 3)
HSQGTFTSDYSKYLDSK*AAHDFVEWLLRA (SEQ ID NO: 13)
H-Aib-QGTFTSDYSKYLDSK*AAHDFVEWLLSA (SEQ ID NO: 14)
H-Aib-QGTFTSDYSKYLDEK*RAKDFIEWLLSA (SEQ ID NO: 15)
H-Aib-QGTFTSDYSKYLDEK*AAKDFIEWLESA (SEQ ID NO: 16)
H-Aib-QGTFTSDYSKYLDSK*AAEDFVEWLESA (SEQ ID NO: 17)
H-Aib-HGTFTSDYSKYLESK*AAEEFIEWLESA (SEQ ID NO: 18)
HSHGTFTSDYSKYLEEK*AAHEFIEWLESA (SEQ ID NO: 19)
H-Aib-HGTFTSDYSKYLEEK*AAHEFVEWLESA (SEQ ID NO: 20)
H-Aib-QGTFTSDYSKYLEEK*AAKDFIEWLESA (SEQ ID NO: 21)
H-Aib-QGTFTSDYSKYLESK*AAEDFIEWLESA (SEQ ID NO: 22)
HSQGTFTSDYSKYLEEK*AAKDFIEWLESA (SEQ ID NO: 23)
H-Aib-QGTFTSDYSKYLESK*AAHDFVEWLESA (SEQ ID NO: 24)
H-Aib-QGTFTSDYSKYLESK*AAEDFVEWLESA (SEQ ID NO: 25)
H-DSer-QGTFTSDYSKYLDEK*AAKDFIEWLESA
``` where "*" indicates the position of a lipohilic or polymeric substituent, particularly a lipophilic substituent.

The compound of the invention may have the formula:

```
                                                  (SEQ ID NO: 1)
H-H-Aib-QGTFTSDYSKYLDSK*AAHDFVEWLLS-OH (SEQ ID NO: 2)
H-HSQGTFTSDYSKYLDSK*AAHDFVEWLLSA-OH (SEQ ID NO: 4)
H-H-Aib-QGTFTSDYSKYLDEK*AAKDFIEWLLSA-NH2

(SEQ ID NO: 5)
H-H-Aib-QGTFTSDYSKYLDSK*AAHDFVEWLESA-NH2

(SEQ ID NO: 6)
H-HSQGTFTSDYSRYLDSK*AAEDFVEWLLRA-NH2

(SEQ ID NO: 7)
H-HSQGTFTSDYSKYLDSK*AAEDFVEWLLRA-NH2

(SEQ ID NO: 8)
H-HSQGTFTSDYSKYLDSK*AAHDFVEWLLS-NH2

(SEQ ID NO: 9)
H-HSQGTFTSDYSKYLDSK*AAHDFVEWLLR-OH (SEQ ID NO: 10)
H-HSQGTFTSDYSKYLDEK*AAHEFVEWLESA-NH2

(SEQ ID NO: 11)
H-H-Aib-QGTFTSDYSKYLDEK*RAKDFIEWLLS-OH (SEQ ID NO: 12)
H-HSQGTFTSDYSRYLDSK*AAHDFVEWLLSA-NH2

(SEQ ID NO: 3)
H-HSQGTFTSDYSKYLDSK*AAHDFVEWLLRA-OH (SEQ ID NO: 13)
H-H-Aib-QGTFTSDYSKYLDSK*AAHDFVEWLLSA-OH (SEQ ID NO: 14)
H-H-Aib-QGTFTSDYSKYLDEK*RAKDFIEWLLSA-OH (SEQ ID NO: 15)
H-H-Aib-QGTFTSDYSKYLDEK*AAKDFIEWLESA-NH2

(SEQ ID NO: 16)
H-H-Aib-QGTFTSDYSKYLDSK*AAEDFVEWLESA-NH2

(SEQ ID NO: 17)
H-H-Aib-HGTFTSDYSKYLESK*AAEEFIEWLESA-OH (SEQ ID NO: 18)
H-HSHGTFTSDYSKYLEEK*AAHEFIEWLESA-OH (SEQ ID NO: 19)
H-H-Aib-HGTFTSDYSKYLEEK*AAHEFVEWLESA-NH2

(SEQ ID NO: 20)
H-H-Aib-QGTFTSDYSKYLEEK*AAKDFIEWLESA-NH2

(SEQ ID NO: 21)
H-H-Aib-QGTFTSDYSKYLESK*AAEDFIEWLESA-NH2

(SEQ ID NO: 22)
H-HSQGTFTSDYSKYLEEK*AAKDFIEWLESA-NH2

(SEQ ID NO: 23)
H-H-Aib-QGTFTSDYSKYLESK*AAHDFVEWLESA-NH2

(SEQ ID NO: 24)
H-H-Aib-QGTFTSDYSKYLESK*AAEDFVEWLESA-NH2

(SEQ ID NO: 25)
H-H-DSer-QGTFTSDYSKYLDEK*AAKDFIEWLESA-NH2
``` or may be a pharmaceutically acceptable salt or solvate thereof.

In certain embodiments, X has the formula:

```
                                                  (SEQ ID NO: 1)
H-Aib-QGTFTSDYSKYLDS-K(Hexadecanoyl-isoGlu)-
AAHDFVEWLLS (SEQ ID NO: 2)
HSQGTFTSDYSKYLDS-K(Hexadecanoyl-isoGlu)-
AAHDFVEWLLSA (SEQ ID NO: 4)
H-Aib-QGTFTSDYSKYLDE-K(Hexadecanoyl-isoGlu)-
AAKDFIEWLLSA (SEQ ID NO: 5)
H-Aib-QGTFTSDYSKYLDS-K(Hexadecanoyl-isoGlu)-
AAHDFVEWLESA
```

(SEQ ID NO: 6)
HSQGTFTSDYSRYLDS-K(Hexadecanoyl-isoGlu)-AAEDFVEWLLRA (SEQ ID NO: 7)
HSQGTFTSDYSKYLDS-K(Hexadecanoyl-isoGlu)-AAEDFVEWLLRA (SEQ ID NO: 8)
HSQGTFTSDYSKYLDS-K(Hexadecanoyl-isoGlu)-AAHDFVEWLLS (SEQ ID NO: 9)
HSQGTFTSDYSKYLDS-K(Hexadecanoyl-isoGlu)-AAHDFVEWLLR (SEQ ID NO: 10)
HSQGTFTSDYSKYLDE-K(Hexadecanoyl-isoGlu)-AAHEFVEWLESA (SEQ ID NO: 11)
H-Aib-QGTFTSDYSKYLDE-K(Hexadecanoyl-isoGlu)-RAKDFIEWLLS (SEQ ID NO: 12)
HSQGTFTSDYSRYLDS-K(Hexadecanoyl-isoGlu)-AAHDFVEWLLSA (SEQ ID NO: 3)
HSQGTFTSDYSKYLDS-K(Hexadecanoyl-isoGlu)-AAHDFVEWLLRA (SEQ ID NO: 13)
H-Aib-QGTFTSDYSKYLDS-K(Hexadecanoyl-isoGlu)-AAHDFVEWLLSA (SEQ ID NO: 14)
H-Aib-QGTFTSDYSKYLDE-K(Hexadecanoyl-isoGlu)-RAKDFIEWLLSA (SEQ ID NO: 15)
H-Aib-QGTFTSDYSKYLDE-K(Hexadecanoyl-isoGlu)-AAKDFIEWLESA (SEQ ID NO: 16)
H-Aib-QGTFTSDYSKYLDS-K(Hexadecanoyl-isoGlu)-AAEDFVEWLESA (SEQ ID NO: 17)
H-Aib-HGTFTSDYSKYLES-K(Hexadecanoyl-isoGlu)-AAEEFIEWLESA (SEQ ID NO: 18)
HSHGTFTSDYSKYLEE-K(Hexadecanoyl-isoGlu)-AAHEFIEWLESA (SEQ ID NO: 19)
H-Aib-HGTFTSDYSKYLEE-K(Hexadecanoyl-isoGlu)-AAHEFVEWLESA (SEQ ID NO: 20)
H-Aib-QGTFTSDYSKYLEEK-(Hexadecanoyl-isoGlu)-AAKDFIEWLESA (SEQ ID NO: 21)
H-Aib-QGTFTSDYSKYLES-K(Hexadecanoyl-isoGlu)-AAEDFIEWLESA (SEQ ID NO: 22)
HSQGTFTSDYSKYLEE-K(Hexadecanoyl-isoGlu)-AAKDFIEWLESA (SEQ ID NO: 23)
H-Aib-QGTFTSDYSKYLES-K(Hexadecanoyl-isoGlu)-AAHDFVEWLESA (SEQ ID NO: 24)
H-Aib-QGTFTSDYSKYLES-K(Hexadecanoyl-isoGlu)-AAEDFVEWLESA (SEQ ID NO: 25)
H-DSer-QGTFTSDYSKYLDE-K(Hexadecanoyl-isoGlu)-AAKDFIEWLESA The compound of the invention may be:

```
H-H-Aib-QGTFTSDYSKYLDS-K(Hexadecanoyl-isoGlu)-AAHDFVEWLLS-OH    (Compound 1)(SEQ ID NO: 1)

H-HSQGTFTSDYSKYLDS-K(Hexadecanoyl-isoGlu)-AAHDFVEWLLSA-OH       (Compound 2)(SEQ ID NO: 2)

H-H-Aib-QGTFTSDYSKYLDE-K(Hexadecanoyl-isoGlu)-AAKDFIEWLLSA-NH2  (Compound 4)(SEQ ID NO: 4)

H-H-Aib-QGTFTSDYSKYLDS-K(Hexadecanoyl-isoGlu)-AAHDFVEWLESA-NH2  (Compound 5)(SEQ ID NO: 5)

H-HSQGTFTSDYSRYLDS-K(Hexadecanoyl-isoGlu)-AAEDFVEWLLRA-NH2      (Compound 6)(SEQ ID NO: 6)

H-HSQGTFTSDYSKYLDS-K(Hexadecanoyl-isoGlu)-AAEDFVEWLLRA-NH2      (Compound 7)(SEQ ID NO: 7)

H-HSQGTFTSDYSKYLDS-K(Hexadecanoyl-isoGlu)-AAHDFVEWLLS-NH2       (Compound 8)(SEQ ID NO: 8)

H-HSQGTFTSDYSKYLDS-K(Hexadecanoyl-isoGlu)-AAHDFVEWLLR-OH        (Compound 9)(SEQ ID NO: 9)

H-HSQGTFTSDYSKYLDE-K(Hexadecanoyl-isoGlu)-AAHEFVEWLESA-NH2      (Compound 10)(SEQ ID NO: 10)

H-H-Aib-QGTFTSDYSKYLDE-K(Hexadecanoyl-isoGlu)-RAKDFIEWLLS-OH    (Compound 11)(SEQ ID NO: 11)

H-HSQGTFTSDYSRYLDS-K(Hexadecanoyl-isoGlu)-AAHDFVEWLLSA-NH2      (Compound 12)(SEQ ID NO: 12)

H-HSQGTFTSDYSKYLDS-K(Hexadecanoyl-isoGlu)-AAHDFVEWLLRA-OH       (Compound 3)(SEQ ID NO: 3)
```

```
H-H-Aib-QGTFTSDYSKYLDS-K(Hexadecanoyl-isoGlu)-AAHDFVEWLLSA-OH  (Compound 13)(SEQ ID NO: 13)

H-H-Aib-QGTFTSDYSKYLDE-K(Hexadecanoyl-isoGlu)-RAKDFIEWLLSA-OH  (Compound 14)(SEQ ID NO: 14)

H-H-Aib-QGTFTSDYSKYLDE-K(Hexadecanoyl-isoGlu)-AAKDFIEWLESA-NH₂ (Compound 15)(SEQ ID NO: 15)

H-H-Aib-QGTFTSDYSKYLDS-K(Hexadecanoyl-isoGlu)-AAEDFVEWLESA-NH₂ (Compound 16)(SEQ ID NO: 16)

H-Aib-HGTFTSDYSKYLES-K(Hexadecanoyl-isoGlu)-AAEEFIEWLESA-OH    (Compound 17)(SEQ ID NO: 17)

H-HSHGTFTSDYSKYLEE-K(Hexadecanoyl-isoGlu)-AAHEFIEWLESA-OH      (Compound 18)(SEQ ID NO: 18)

H-H-Aib-HGTFTSDYSKYLEE-K(Hexadecanoyl-isoGlu)-AAHEFVEWLESA-NH₂ (Compound 19)(SEQ ID NO: 19)

H-H-Aib-QGTFTSDYSKYLEE-K(Hexadecanoyl-isoGlu)-AAKDFIEWLESA-NH₂ (Compound 20)(SEQ ID NO: 20)

H-H-Aib-QGTFTSDYSKYLES-K(Hexadecanoyl-isoGlu)-AAEDFIEWLESA-NH₂ (Compound 21)(SEQ ID NO: 21)

H-HSQGTFTSDYSKYLEE-K(Hexadecanoyl-isoGlu)-AAKDFIEWLESA-NH₂     (Compound 22)(SEQ ID NO: 22)

H-H-Aib-QGTFTSDYSKYLES-K(Hexadecanoyl-isoGlu)-AAHDFVEWLESA-NH₂ (Compound 23)(SEQ ID NO: 23)

H-H-Aib-QGTFTSDYSKYLES-K(Hexadecanoyl-isoGlu)-AAEDFVEWLESA-NH₂ (Compound 24)(SEQ ID NO: 24)

H-H-DSer-QGTFTSDYSKYLDE-K(Hexadecanoyl-isoGlu)-AAKDFIEWLESA-   (Compound 25)(SEQ ID NO: 25)
NH₂
``` or may be a pharmaceutically acceptable salt or solvate thereof.

For those peptide sequences X or X—Z composed exclusively of naturally-occurring amino acids, the invention further provides a nucleic acid (which may be DNA or RNA) encoding a peptide X or X—Z as defined herein. Also provided is an expression vector comprising such a nucleic acid, and a host cell containing such a nucleic acid or expression vector. The host cell is typically capable of expressing and optionally secreting the encoded peptide X or X—Z.

The compounds of the invention are glucagon analogue peptides. References herein to a glucagon analogue peptide should be construed as references to a compound of the invention or to a peptide X or X—Z as the context requires. Reference to a compound of the invention should be taken to include any pharmaceutically acceptable salt (e.g. an acetate or chloride salt) or solvate thereof, unless otherwise stated or excluded by context.

The invention provides a composition comprising a compound of the invention as defined herein (including pharmaceutically acceptable salts or solvates thereof, as already described), a nucleic acid encoding a peptide X or X—Z, an expression vector comprising such a nucleic acid, or a host cell containing such a nucleic acid or expression vector, in admixture with a carrier. In preferred embodiments, the composition is a pharmaceutical composition and the carrier is a pharmaceutically acceptable carrier. The glucagon analogue peptide may be in the form of a pharmaceutically acceptable salt of the glucagon analogue.

The compounds described herein find use, inter alia, in preventing weight gain or promoting weight loss. By "preventing" is meant inhibiting or reducing when compared to the absence of treatment, and is not necessarily meant to imply complete cessation of weight gain. The peptides may cause a decrease in food intake and/or increased energy expenditure, resulting in the observed effect on body weight. Independently of their effect on body weight, the compounds of the invention may have a beneficial effect on glucose control and/or on circulating cholesterol levels, being capable of lowering circulating LDL levels and increasing HDL/LDL ratio. Thus the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for the prevention of conditions caused or characterised by inadequate glucose control or dyslipidaemia (e.g. elevated LDL levels or reduced HDL/LDL ratio), diabetes (especially Type 2 diabetes), metabolic syndrome, hypertension, atherogenic dyslipidemia, atherosclerosis, arteriosclerosis, coronary heart disease, peripheral artery disease, stroke or microvascular disease. Their effects in these conditions may be as a result of or associated with their effect on body weight, or may be independent thereof.

The invention also provides a compound of the invention for use in a method of medical treatment, particularly for use in a method of treatment of a condition as described above.

The invention also provides the use of a compound of the invention in the preparation of a medicament for the treatment of a condition as described above.

The compound of the invention may be administered as part of a combination therapy with an agent for treatment of diabetes, obesity, dyslipidaemia or hypertension.

In such cases, the two active agents may be given together or separately, and as part of the same pharmaceutical formulation or as separate formulations.

Thus the compound of the invention can be used in combination with an anti-diabetic agent including but not limited to a biguanide (e.g. metformin), a sulfonylurea, a meglitinide or glinide (e.g. nateglinide), a DPP-IV inhibitor, a glitazone, an insulin, or an insulin analogue. Examples of insulin analogues include but are not limited to Lantus™, Novorapid™, Humalog™, Novomix™, Actraphane HM™, Levemir™ and Apidra™.

The compound can further be used in combination with an anti-obesity agent including but not limited to a glucagon-like peptide receptor 1 agonist, peptide YY or analogue thereof, cannabinoid receptor 1 antagonist, lipase inhibitor, melanocortin receptor 1 agonist, or melanin concentrating hormone receptor 1 antagonist.

The compound can further be used in combination with an anti-hypertension agent including but not limited to an angiotensin-converting enzyme inhibitor, angiotensin II receptor blocker, diuretic, beta-blocker, or calcium channel blocker.

The compound can be used in combination with an anti-dyslipidaemia agent including but not limited to a statin, a fibrate, a niacin or a cholesterol absorption inhibitor.

Thus the invention further provides a composition or therapeutic kit comprising a compound of the invention and for example an anti-diabetic agent, anti-obesity agent, anti-hypertension agent or anti-dyslipidaemia agent as described above. Also provided is such a composition or therapeutic kit for use in a method of medical treatment, especially for treatment of a condition as described above.

The compound of the invention may be made by synthetic chemistry. Accordingly the invention provides a method of synthesis of a compound of the invention.

As already described, the invention extends to nucleic acids encoding the peptide sequence X or X—Z, as well as expression vectors comprising the above-described nucleic acid sequence (optionally operably linked to sequences to direct its expression) and host cells containing the nucleic acids or expression vectors. Preferably the host cells are capable of expressing and optionally secreting the compound of the invention.

The present invention provides a method of producing a compound of the invention, the method comprising culturing the host cells under conditions suitable for expressing the peptide sequence X or X—Z and purifying the compound thus produced. This is particularly useful where the peptide contains only naturally-occurring amino acids.

Where the compound of the invention contains one or more non-naturally-occurring amino acids, the method may comprise expressing a peptide sequence containing one or more differences from the sequence X or X—Z, optionally purifying the compound thus produced, and adding or modifying one or more amino acids to produce a compound of the invention or a compound comprising the amino acid sequence X or X—Z.

Whichever method is used to produce the compound of the invention, it may comprise one or more further steps of modifying the sequence X or X—Z, especially to introduce one or more lipophilic and/or polymeric moieties as defined elsewhere in this specification.

The invention further provides a nucleic acid of the invention, an expression vector of the invention, or a host cell capable of expressing and optionally secreting a compound of the invention, for use in a method of medical treatment. It will be understood that the nucleic acid, expression vector and host cells may be used for treatment of any of the disorders described herein which may be treated with the compounds of the invention themselves. References to a therapeutic composition comprising a compound of the invention, administration of a compound of the invention, or any therapeutic use thereof, should therefore be construed to encompass the equivalent use of a nucleic acid, expression vector or host cell of the invention, except where the context demands otherwise.

DETAILED DESCRIPTION OF THE INVENTION

Throughout this specification, the conventional one letter and three letter codes for naturally occurring amino acids are used, as well as generally accepted three letter codes for other amino acids, such as Aib (α-aminoisobutyric acid), Hse (homoserine), Orn (ornithine), Dbu (2,4-diaminobutyric acid), Dpr (2,3-diaminopropanoic acid).

Glucagon is a 29-amino acid peptide that corresponds to amino acids 53 to 81 of pre-proglucagon and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 26). Oxyntomodulin (OXM) is a 37 amino acid peptide which includes the complete 29 amino acid sequence of glucagon with an octapeptide carboxyterminal extension (amino acids 82 to 89 of pre-proglucagon, having the sequence Lys-Arg-Asn-Arg-Asn-Asn-Ile-Ala (SEQ ID NO: 27) and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala) (SEQ ID NO: 28). The major biologically active fragment of GLP-1 is produced as a 30-amino acid, C-terminally amidated peptide that corresponds to amino acids 98 to 127 of pre-proglucagon.

The term "native glucagon" thus refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO: 26).

Amino acids within the sequence X of the compounds of the invention can be considered to be numbered consecutively from 1 to 29 in the conventional N-terminal to C-terminal direction. Reference to a "position" within X should be construed accordingly, as should reference to positions within native human glucagon and other molecules.

A compound of the invention may comprise a C-terminal peptide sequence Z of 1-20 amino acids, for example to stabilise the conformation and/or secondary structure of the glucagon analogue peptide, and/or to render the glucagon analogue peptide more resistant to enzymatic hydrolysis, e.g. as described in WO99/46283.

When present, Z represents a peptide sequence of 1-20 amino acid residues, e.g. in the range of 1-15, more preferably in the range of 1-10, in particular in the range of 1-7 amino acid residues, e.g., 1, 2, 3, 4, 5, 6 or 7 amino acid residues, such as 6 amino acid residues. Each of the amino acid residues in the peptide sequence Z may independently be selected from Ala, Leu, Ser, Thr, Tyr, Cys, Glu, Lys, Arg, Dbu (2,4-diaminobutyric acid), Dpr (2,3-diaminopropanoic acid) and Orn (ornithine). Preferably, the amino acid residues are selected from Ser, Thr, Tyr, Glu, Lys, Arg, Dbu, Dpr and Orn, more preferably selected exclusively from Glu, Lys, and Cys. The above-mentioned amino acids may have either D- or L-configuration, which in certain embodiments, have an L-configuration. Particularly preferred sequences Z are sequences of four, five, six or seven consecutive lysine residues (i.e. $Lys_3$, $Lys_4$, $Lys_5$, $Lys_6$ or $Lys_7$), and particularly five or six consecutive lysine residues. Other exemplary sequences of Z are shown in WO 01/04156. Alternatively the C-terminal residue of the sequence Z may be a Cys residue. This may assist in modification (e.g. PEGylation, or conjugation to albumin) of the compound. In such embodiments, the sequence Z may, for example, be only one amino acid in length (i.e. Z=Cys) or may be two, three, four, five, six or even more amino acids in length. The other amino acids therefore serve as a spacer between the peptide X and the terminal Cys residue.

The peptide sequence Z has no more than 25% sequence identity with the corresponding sequence of the IP-1 portion of human OXM (which has the sequence Lys-Arg-Asn-Arg-Asn-Asn-Ile-Ala).

"Percent (%) amino acid sequence identity" of a given peptide or polypeptide sequence with respect to another polypeptide sequence (e.g. IP-1) is calculated as the percentage of amino acid residues in the given peptide sequence that are identical with correspondingly positioned amino acid residues in the corresponding sequence of that other polypeptide when the two are aligned with one another, introducing gaps for optimal alignment if necessary. % identity values may be determined using WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Thus, when Z is aligned optimally with the 8 amino acids of IP-1, it has no more than two amino acids which are identical with the corresponding amino acids of IP-1.

In certain embodiments, Z is absent.

One or more of the amino acid side chains in the compound of the invention may be conjugated to a lipophilic substituent. The lipophilic substituent may be covalently bonded to an atom in the amino acid side chain, or alternatively may be conjugated to the amino acid side chain by a spacer. A lipophilic substituent may be conjugated to a side chain of an amino acid which is part of the peptide X, and/or to a side chain of an amino acid which is part of the peptide Z.

Without wishing to be bound by any particular theory, it is thought that the lipophilic substituent binds albumin in the blood stream, thus shielding the compounds of the invention from enzymatic degradation and thereby enhancing the half-life of the compounds. It may also modulate the potency of the compound, e.g. with respect to the glucagon receptor and/or the GLP-1 receptor.

In certain embodiments, only one amino acid side chain is conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different.

The lipophilic substituent may comprise or consist of a lipophilic moiety $Z^1$ which may be covalently bonded directly to an atom in the amino acid side chain, or alternatively may be conjugated to the amino acid side chain by a spacer $Z^2$.

The term "conjugated" is used here to describe the physical attachment of one identifiable chemical moiety to another, and the structural relationship between such moieties. It should not be taken to imply any particular method of synthesis.

The lipophilic moiety may be attached to the amino acid side chain or to the spacer via an ester, a sulphonyl ester, a thioester, an amide, a carbamate, a urea or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic moiety may include a hydrocarbon chain having 4 to 30 C atoms. Preferably it has at least 8 or 12 C atoms, and preferably it has 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom.

Most preferably the hydrocarbon chain is substituted with acyl, and accordingly the hydrocarbon chain may be part of an alkanoyl group, for example palmitoyl, caproyl, lauroyl, myristoyl or stearoyl.

Accordingly, the lipophilic moiety may have the formula shown below:

A may be, for example, an acyl group, a sulphonyl group, NH, N-alkyl, an O atom or an S atom, preferably acyl. n is an integer from 3 to 29, preferably from 7 to 25, more preferred 11 to 21, even more preferred 15 to 19.

The hydrocarbon chain may be further substituted. For example, it may be further substituted with up to three substituents selected from $NH_2$, OH and COOH, especially at the free end of the molecule distal from the spacer or peptide. For example, it may comprise a free carboxylic acid group.

If the hydrocarbon chain is further substituted, preferably it is further substituted with only one substituent. Alternatively or additionally, the hydrocarbon chain may include a cycloalkane or heterocycloalkane, for example as shown below:

Preferably the cycloalkane or heterocycloalkane is a six-membered ring. Most preferably, it is piperidine.

Alternatively, the lipophilic moiety may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As mentioned above, the lipophilic moiety may be conjugated to the amino acid side chain by a spacer. When present, the spacer is attached to the lipophilic moiety and to the amino acid side chain. The spacer may be attached to the lipophilic moiety and to the amino acid side chain independently by an ester, a sulphonyl ester, a thioester, an amide, a carbamate, a urea or a sulphonamide. Accordingly, it may include two moieties independently selected from acyl, sulphonyl, an N atom, an O atom or an S atom. The spacer may have the formula:

wherein B and D are each independently selected from acyl, sulphonyl, NH, N-alkyl, an O atom and an S atom, preferably from acyl and NH. Preferably, n is an integer from 1 to 10, preferably from 1 to 5. The spacer may be further substituted with one or more substituents selected from $C_{0-6}$ alkyl, $C_{0-6}$ alkyl amine, $C_{0-6}$ alkyl hydroxy and $C_{0-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic moiety as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalised side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gln, Asn, α-Glu, γ-Glu, Asp, Ser Thr, Gaba, Aib, β-Ala, 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from γ-Glu, Gaba, β-Ala and α-Glu.

A lipophilic substituent may be conjugated to any amino acid side chain in a compound of the invention. Preferably, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. Preferably, the lipophilic substituent is conjugated to Lys. An amino acid shown as Lys in the formulae provided herein may be replaced by, e.g., Dbu, Dpr or Orn where a lipophilic substituent is added.

An example of a lipophilic substituent comprising lipophilic moiety and spacer is shown in the formula below:

listed e.g. in "Comprehensive Organic Transformations, A Guide to Functional Group Preparations", 2nd edition, Larock, R. C.; Wiley-VCH: New York, 1999. Such transformations may take place at any suitable stage during the synthesis process.

The polymeric moiety is preferably water-soluble (amphiphilic or hydrophilic), non-toxic, and pharmaceutically inert. Suitable polymeric moieties include polyethylene glycol (PEG), homo- or co-polymers of PEG, a monomethyl-substituted polymer of PEG (mPEG), and polyoxyethylene glycerol (POG). See, for example, *Int. J. Hematology* 68:1 (1998); *Bioconjugate Chem.* 6:150 (1995); and *Crit. Rev. Therap. Drug Carrier Sys.* 9:249 (1992).

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57; Tsukada, et al. (1984), J. Natl. Cancer Inst., vol 73: 721-729; and Pratesi, et al. (1985), Br. J. Cancer, vol. 52: 841-848).

The polymeric moiety may be straight-chain or branched. It may have a molecular weight of 500-40,000 Da, for example 500-10,000 Da, 1000-5000 Da, 10,000-20,000 Da, or 20,000-40,000 Da.

A compound of the invention may comprise two or more such moieties, in which case the total molecular weight of all such moieties will generally fall within the ranges provided above.

The polymeric moiety may be coupled (by covalent linkage) to an amino, carboxyl or thiol group of an amino acid side chain. Preferred examples are the thiol group of Cys

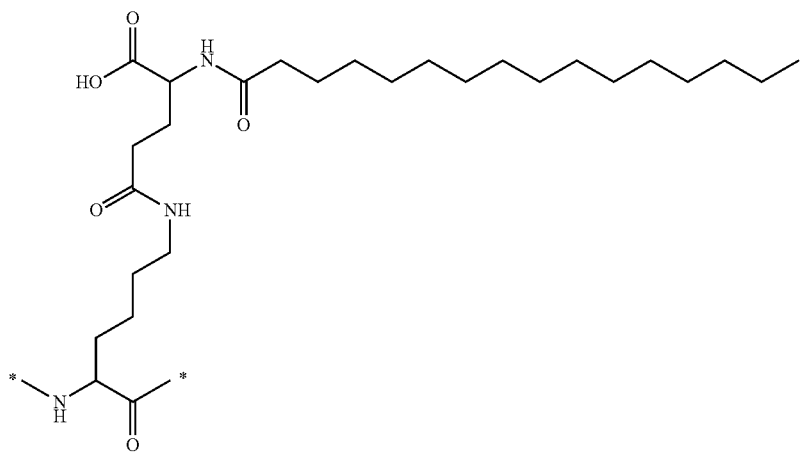 [SMILES: CCCCCCCCCCCCCCCC(=O)NC(CCC(=O)NCCCCC(NC)C(C)=O)C(=O)O]

Here, a Lys residue in the compound of the present invention is covalently attached to γ-Glu (the spacer) via an amide moiety. Palmitoyl (i.e. hexadecanoyl) is covalently attached to the γ-Glu spacer via an amide moiety, thus creating a hexadecanoyl-isoGlu group.

Alternatively or additionally, one or more amino acid side chains in the compound of the invention may be conjugated to a polymeric moiety, for example, in order to increase solubility and/or half-life in vivo (e.g. in plasma) and/or bioavailability. Such modification is also known to reduce clearance (e.g. renal clearance) of therapeutic proteins and peptides.

The skilled reader will be well aware of suitable techniques that can be used to perform the coupling reactions with spacer and lipophilic moiety using general synthetic methodology residues and the epsilon amino group of Lys residues. The carboxyl groups of Asp and Glu residues may also be used.

The skilled reader will be well aware of suitable techniques that can be used to perform the coupling reaction. For example, a PEG moiety carrying a methoxy group can be coupled to a Cys thiol group by a maleimido linkage using reagents commercially available from Nektar Therapeutics. See also WO 2008/101017, and the references cited above, for details of suitable chemistry.

Peptide Synthesis

The compounds of the present invention may be manufactured either by standard synthetic methods, recombinant expression systems, or any other state of the art method. Thus the glucagon analogues may be synthesized in a number of ways, including, for example, a method which comprises:

(a) synthesizing the peptide by means of solid-phase or liquid-phase methodology, either stepwise or by fragment assembly, and isolation and purifying of the final peptide product; or
(b) expressing a nucleic acid construct that encodes the peptide in a host cell, and recovering the expression product from the host cell or culture medium; or
(c) effecting cell-free in vitro expression of a nucleic acid construct that encodes the peptide, and recovering the expression product;
or any combination of methods of (a), (b), and (c) to obtain fragments of the peptide, subsequently ligating the fragments to obtain the peptide, and recovering the peptide.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments of the invention will normally be inserted in suitable vectors to form cloning or expression vectors carrying the nucleic acid fragments of the invention; such novel vectors are also part of the invention. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

In general outline, an expression vector comprises the following features in the 5'3' direction and in operable linkage: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the compound of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment are useful embodiments of the invention; they can be used for small-scale or large-scale preparation of the peptides of the invention.

When producing the peptide of the invention by means of transformed cells, it is convenient, although far from essential, that the expression product is secreted into the culture medium.

Efficacy

Binding of the relevant compounds to GLP-1 or glucagon (Glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may employ the human glucagon receptor (Glucagon-R) having primary accession number GI:4503947 and/or the human glucagon-like peptide 1 receptor (GLP-1R) having primary accession number GI:166795283. (in that where sequences of precursor proteins are referred to, it should of course be understood that assays may make use of the mature protein, lacking the signal sequence).

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$[GLP-1] lower than the $EC_{50}$[GLP-1] of glucagon in a particular assay may be considered to have higher GLP-1 receptor agonist potency than glucagon.

The compounds described in this specification are typically GluGLP-1 dual agonists, as determined by the observation that they are capable of stimulating cAMP formation at both the glucagon receptor and the GLP-1 receptor. The stimulation of each receptor can be measured in independent assays and afterwards compared to each other.

By comparing the $EC_{50}$ value for the GLP-1 receptor ($EC_{50}$ [GLP-1-R]) with the $EC_{50}$ value for the Glucagon receptor, ($EC_{50}$ [GlucagonR]) for a given compound. the relative GLP-1R selectivity can be calculated as follows:

$$\text{Relative GLP-1R selectivity [compound]} = (EC_{50}[\text{GLP-1R}])/(EC_{50}[\text{Glucagon-R}])$$

The term "$EC_{50}$" stands for the half maximal Effective Concentration, typically at a particular receptor, or on the level of a particular marker for receptor function, and can refer to an inhibitory or an antagonistic activity, depending on the specific biochemical context.

Without wishing to be bound by any particular theory, a compound's relative selectivity may allow its effect on the GLP-1 or glucagon receptor to be compared directly to its effect on the other receptor. For example, the higher a compound's relative GLP-1 selectivity is, the more effective that compound may be on the GLP-1 receptor as compared to the glucagon receptor. Typically the results are compared for glucagon and GLP-1 receptors from the same species, e.g. human glucagon and GLP-1 receptors, or murine glucagon and GLP-1 receptors.

The compounds of the invention may have a higher relative GLP-1R selectivity than human glucagon in that for a particular level of glucagon-R agonist activity, the compound may display a higher level of GLP-1R agonist activity (i.e. greater potency at the GLP-1 receptor) than glucagon. It will be understood that the absolute potency of a particular compound at the glucagon and GLP-1 receptors may be higher, lower or approximately equal to that of native human glucagon, as long as the appropriate relative GLP-1R selectivity is achieved.

Nevertheless, the compounds of this invention may have a lower $EC_{50}$ [GLP-1R] than human glucagon. The compounds may have a lower $EC_{50}$[GLP-1-R] than glucagon while maintaining an $EC_{50}$ [Glucagon-R] that is less than 10-fold higher than that of human glucagon, less than 5-fold higher than that of human glucagon, or less than 2-fold higher than that of human glucagon.

The compounds of the invention may have an $EC_{50}$ [Glucagon-R] that is less than two-fold that of human glucagon. The compounds may have an $EC_{50}$ [Glucagon-R] that is less than two-fold that of human glucagon and have an $EC_{50}$ [GLP-1R] that is less than half that of human glucagon, less than a fifth of that of human glucagon, or less than a tenth of that of human glucagon.

The relative GLP-1R selectivity of the compounds may be between 0.05 and 20. For example, the compounds may have a relative selectivity of 0.05-0.20, 0.1-0.30, 0.2-0.5, 0.3-0.7, or 0.5-1.0; 1.0-2.0, 1.5-3.0, 2.0-4.0 or 2.5-5.0; or 0.05-20, 0.075-15, 0.1-10, 0.15-5, 0.75-2.5 or 0.9-1.1.

In certain embodiments, it may be desirable that $EC_{50}$ of any given compound for both the Glucagon-R and GLP-1R, e.g. for the human glucagon and GLP-1 receptors, should be less than 1 nM.

Therapeutic Uses

The compounds of the invention may provide attractive treatment and/or prevention options for, inter alia, obesity and metabolic diseases including diabetes, as discussed below.

Diabetes comprises a group of metabolic diseases characterized by hyperglycemia resulting from defects in insulin secretion, insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with long-term damage, dysfunction, and failure of various organs, notably the eyes, kidneys, nerves, heart and blood vessels. Diabetes is classified into type 1 diabetes, type 2 diabetes and gestational diabetes on the basis on pathogenetic characteristics.

Type 1 diabetes accounts for 5-10% of all diabetes cases and is caused by auto-immune destruction of insulin-secreting pancreatic β-cells.

Type 2 diabetes accounts for 90-95% of diabetes cases and is a result of a complex set of metabolic disorders. Type 2 diabetes is the consequence of endogenous insulin production becoming insufficient to maintain plasma glucose levels below the diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor-1 in the blood), and proinflammatory state (e.g., elevated C-reactive protein in the blood).

Conversely, obesity confers an increased risk of developing pre-diabetes, type 2 diabetes as well as e.g. certain types of cancer, obstructive sleep apnea and gall-bladder disease.

Dyslipidaemia is associated with increased risk of cardiovascular disease. High Density Lipoprotein (HDL) is of clinical importance since an inverse correlation exists between plasma HDL concentrations and risk of atherosclerotic disease. The majority of cholesterol stored in atherosclerotic plaques originates from LDL and hence elevated concentrations Low Density Lipoproteins (LDL) is closely associated with atherosclerosis. The HDL/LDL ratio is a clinical risk indictor for atherosclerosis and coronary atherosclerosis in particular.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with the metabolic syndrome are at increased risk of coronary heart disease and other diseases related to other manifestations of arteriosclerosis (e.g., stroke and peripheral vascular disease). The dominant underlying risk factors for this syndrome appear to be abdominal obesity.

Without wishing to be bound by any particular theory, it is believed that the compounds of the invention act as dual agonists both on the human glucagon-receptor and the human GLP1-receptor, abbreviated here as dual GluGLP-1 agonists. The dual agonist may combine the effect of glucagon, e.g. on fat metabolism, with the effect of GLP-1, e.g. on blood glucose levels and food intake. They may therefore act to accelerate elimination of excessive adipose tissue, induce sustainable weight loss, and improve glycaemic control. Dual GluGLP-1 agonists may also act to reduce cardiovascular risk factors such as high cholesterol, high LDL-cholesterol or low HDL/LDL cholesterol ratios.

The compounds of the present invention can therefore be used in a subject in need thereof as pharmaceutical agents for preventing weight gain, promoting weight loss, reducing excess body weight or treating obesity (e.g. by control of appetite, feeding, food intake, calorie intake, and/or energy expenditure), including morbid obesity, as well as associated diseases and health conditions including but not limited to obesity linked inflammation, obesity linked gallbladder disease and obesity induced sleep apnea. The compounds of the invention may also be used for treatment of conditions caused by or associated with impaired glucose control, including metabolic syndrome, insulin resistance, glucose intolerance, pre-diabetes, increased fasting glucose, type 2 diabetes, hypertension, atherosclerois, arteriosclerosis, coronary heart disease, peripheral artery disease and stroke, in a subject in need thereof. Some of these conditions can be associated with obesity. However, the effects of the compounds of the invention on these conditions may be mediated in whole or in part via an effect on body weight, or may be independent thereof.

The synergistic effect of dual GluGLP-1 agonists may also result in reduction of cardiovascular risk factors such as high cholesterol and LDL, which may be entirely independent of their effect on body weight.

Thus the invention provides the use of a compound of the invention in the treatment of a condition as described above, in an individual in need thereof.

The invention also provides a compound of the invention for use in a method of medical treatment, particularly for use in a method of treatment of a condition as described above.

In a preferred aspect, the compounds described may be used in treating diabetes, esp. type 2 diabetes.

In a specific embodiment, the present invention comprises use of a compound for treating diabetes, esp. type 2 diabetes in an individual in need thereof.

In a not less preferred aspect, the compounds described may be used in preventing weight gain or promoting weight loss.

In a specific embodiment, the present invention comprises use of a compound for preventing weight gain or promoting weight loss in an individual in need thereof.

In a specific embodiment, the present invention comprises use of a compound in a method of treatment of a condition caused or characterised by excess body weight, e.g. the treatment and/or prevention of obesity, morbid obesity, morbid obesity prior to surgery, obesity linked inflammation, obesity linked gallbladder disease, obesity induced sleep apnea, prediabetes, diabetes, esp. type 2 diabetes, hypertension, atherogenic dyslipidimia, atherosclerois, arteriosclerosis, coronary heart disease, peripheral artery disease, stroke or microvascular disease in an individual in need thereof.

In another aspect, the compounds described may be used in a method of lowering circulating LDL levels, and/or increasing HDL/LDL ratio.

In a specific embodiment, the present invention comprises use of a compound in a method of lowering circulating LDL levels, and/or increasing HDL/LDL ratio in an individual in need thereof.

In another aspect, the compounds described may be used in a method of lowering circulating triglyceride levels.

Pharmaceutical Compositions

The compounds of the present invention may be formulated as pharmaceutical compositions prepared for storage or administration. Such a composition typically comprises a therapeutically effective amount of a compound of the invention, in the appropriate form, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. The compounds of the present invention may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompass any agents listed in the US Pharmacopeia for use in animals, including humans.

The term "pharmaceutically acceptable salt" refers to a salt of any one of the compounds of the invention. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms (e.g. weight gain, hyperglycemia) when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

Subcutaneous or transdermal modes of administration may be particularly suitable for the compounds described herein.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Combination Therapy

A compound or composition of the invention may be administered as part of a combination therapy with an agent for treatment of obesity, hypertension, dyslipidemia or diabetes.

In such cases, the two active agents may be given together or separately, and as part of the same pharmaceutical formulation or as separate formulations.

Thus a compound or composition of the invention can further be used in combination with an anti-obesity agent, including but not limited to a glucagon-like peptide receptor 1 agonist, peptide YY or analogue thereof, cannabinoid receptor 1 antagonist, lipase inhibitor, melanocortin receptor 1 agonist, or melanin concentrating hormone receptor 1 antagonist.

A compound or composition of the invention can be used in combination with an anti-hypertension agent, including but not limited to an angiotensin-converting enzyme inhibitor, angiotensin II receptor blocker, diuretics, beta-blocker, or calcium channel blocker.

A compound or composition of the invention can be used in combination with a dyslipidaemia agent, including but not limited to a statin, a fibrate, a niacin and/or a cholesterol absorption inhibitor.

Further, a compound or composition of the invention can be used in combination with an anti-diabetic agent, including but not limited to a biguanide (e.g. metformin), a sulfonylurea, a meglitinide or glinide (e.g. nateglinide), a DPP-IV inhibitor, a glitazone, a different GLP-1 agonist, an insulin or an insulin analogue. In a preferred embodiment, the compound or salt thereof is used in combination with insulin or an insulin analogue, DPP-IV inhibitor, sulfonylurea or metformin, particularly sulfonylurea or metformin, for achieving adequate glycemic control. Examples of insulin analogues include but are not limited to Lantus, Novorapid, Humalog, Novomix, and Actraphane HM, Levemir and Apidra.

EXAMPLES

Example 1

General Synthesis of Glucagon Analogues

Solid phase peptide synthesis (SPPS) was performed on a microwave assisted synthesizer using standard Fmoc strategy in NMP on a polystyrene resin (TentaGel S Ram). HATU was used as coupling reagent together with DIPEA as base. Pipiridine (20% in NMP) was used for deprotection. Pseudoprolines: Fmoc-Phe-Thr(psiMe,Mepro)-OH and Fmoc-Asp-Ser (psiMe,Mepro)-OH (purchased from NovaBiochem) were used where applicable.

Abbreviations employed are as follows:
Boc: tert-butyloxycarbonyl
ivDde: 1-(4,4-dimethyl-2,6-dioxocyclohexylidene)$_3$-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EDT: 1,2-ethanedithiol
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane
Cleavage:

The crude peptide was cleaved from the resin by treatment with 95/2.5/2.5% (v/v) TFA/TIS/water at room temperature (r.t.) for 2 hours. For peptides with a methionine in the sequence a mixture of 95/5 (v/v) TFA/EDT was used. Most of the TFA was removed at reduced pressure and the crude peptide was precipitated and washed with diethylether and allowed to dry to constant weight at ambient temperature.

The following compounds were synthesised:

```
H-H-Aib-QGTFTSDYSKYLDS-K(Hexadecanoyl-isoGlu)-AAHDFVEWLLS-OH      (Compound 1)(SEQ ID NO: 1)

H-HSQGTFTSDYSKYLDS-K(Hexadecanoyl-isoGlu)-AAHDFVEWLLSA-OH         (Compound 2)(SEQ ID NO: 2)

H-HSQGTFTSDYSKYLDS-K(Hexadecanoyl-isoGlu)-AAHDFVEWLLRA-OH         (Compound 3)(SEQ ID NO: 3)
```

-continued

| | |
|---|---|
| H-H-Aib-QGTFTSDYSKYLDE-K(Hexadecanoyl-isoGlu)-AAKDFIEWLLSA-NH₂ | (Compound 4)(SEQ ID NO: 4) |
| H-H-Aib-QGTFTSDYSKYLDS-K(Hexadecanoyl-isoGlu)-AAHDFVEWLESA-NH₂ | (Compound 5)(SEQ ID NO: 5) |
| H-HSQGTFTSDYSRYLDS-K(Hexadecanoyl-isoGlu)-AAEDFVEWLLRA-NH₂ | (Compound 6)(SEQ ID NO: 6) |
| H-HSQGTFTSDYSKYLDS-K(Hexadecanoyl-isoGlu)-AAEDFVEWLLRA-NH₂ | (Compound 7)(SEQ ID NO: 7) |
| H-HSQGTFTSDYSKYLDS-K(Hexadecanoyl-isoGlu)-AAHDFVEWLLS-NH₂ | (Compound 8)(SEQ ID NO: 8) |
| H-HSQGTFTSDYSKYLDS-K(Hexadecanoyl-isoGlu)-AAHDFVEWLLR-OH | (Compound 9)(SEQ ID NO: 9) |
| H-HSQGTFTSDYSKYLDE-K(Hexadecanoyl-isoGlu)-AAHEFVEWLESA-NH₂ | (Compound 10)(SEQ ID NO: 10) |
| H-H-Aib-QGTFTSDYSKYLDE-K(Hexadecanoyl-isoGlu)-RAKDFIEWLLS-OH | (Compound 11)(SEQ ID NO: 11) |
| H-HSQGTFTSDYSRYLDS-K(Hexadecanoyl-isoGlu)-AAHDFVEWLLSA-NH₂ | (Compound 12)(SEQ ID NO: 12) |
| H-H-Aib-QGTFTSDYSKYLDS-K(Hexadecanoyl-isoGlu)-AAHDFVEWLLSA-OH | (Compound 13)(SEQ ID NO: 13) |
| H-H-Aib-QGTFTSDYSKYLDE-K(Hexadecanoyl-isoGlu)-RAKDFIEWLLSA-OH | (Compound 14)(SEQ ID NO: 14) |
| H-H-Aib-QGTFTSDYSKYLDE-K(Hexadecanoyl-isoGlu)-AAKDFIEWLESA-NH₂ | (Compound 15)(SEQ ID NO: 15) |
| H-H-Aib-QGTFTSDYSKYLDS-K(Hexadecanoyl-isoGlu)-AAEDFVEWLESA-NH₂ | (Compound 16)(SEQ ID NO: 16) |
| H-H-Aib-HGTFTSDYSKYLES-K(Hexadecanoyl-isoGlu)-AAEEFIEWLESA-OH | (Compound 17)(SEQ ID NO: 17) |
| H-HSHGTFTSDYSKYLEE-K(Hexadecanoyl-isoGlu)-AAHEFIEWLESA-OH | (Compound 18)(SEQ ID NO: 18) |
| H-H-Aib-HGTFTSDYSKYLEE-K(Hexadecanoyl-isoGlu)-AAHEFVEWLESA-NH₂ | (Compound 19)(SEQ ID NO: 19) |
| H-H-Aib-QGTFTSDYSKYLEE-K(Hexadecanoyl-isoGlu)-AAKDFIEWLESA-NH₂ | (Compound 20)(SEQ ID NO: 20) |
| H-H-Aib-QGTFTSDYSKYLEE-K(Hexadecanoyl-isoGlu)-AAEDFIEWLESA-NH₂ | (Compound 21)(SEQ ID NO: 21) |
| H-HSQGTFTSDYSKYLEE-K(Hexadecanoyl-isoGlu)-AAKDFIEWLESA-NH₂ | (Compound 22)(SEQ ID NO: 22) |
| H-H-Aib-QGTFTSDYSKYLES-K(Hexadecanoyl-isoGlu)-AAHDFVEWLESA-NH₂ | (Compound 23)(SEQ ID NO: 23) |
| H-H-Aib-QGTFTSDYSKYLES-K(Hexadecanoyl-isoGlu)-AAEDFVEWLESA-NH₂ | (Compound 24)(SEQ ID NO: 24) |
| H-H-DSer-QGTFTSDYSKYLDE-K(Hexadecanoyl-isoGlu)-AAKDFIEWLESA-NH₂ | (Compound 25)(SEQ ID NO: 25) |

Example 2

General Synthesis of Acylated Glucagon Analogues

The peptide backbone was synthesized as described above for the general synthesis of glucagon analogues, with the exception that it was acylated on the side chain of a lysine residue with the peptide still attached to the resin and fully protected on the side chain groups, except the epsilon-amine on the lysine to be acylated. The lysine to be acylated was incorporated with the use of Fmoc-Lys(ivDde)-OH or Fmoc-Lys(Dde)-OH. The N-terminus of the peptide was protected with a Boc group using Boc₂O in NMP. While the peptide was still attached to the resin, the ivDde protecting group was selectively cleaved using 5% hydrazine hydrate in NMP. The unprotected lysine side chain was then first coupled with a spacer amino acid like Fmoc-Glu-OtBu, which was subsequently deprotected with piperidine and acylated with a fatty acid using standard peptide coupling methodology as described above. Alternatively, the histidine at the N-terminal may be incorporated from the beginning as Boc-His(Boc)-OH. Cleavage from the resin and purification were performed as described above.

Example 3

Glucagon Receptor and GLP-1-Receptor Efficacy Assays

The cDNA encoding either the human glucagon receptor (Glucagon-R) (primary accession number P47871) or the human glucagon-like peptide 1 receptor (GLP-1R) (primary accession number P43220) were synthesized and cloned into a mammalian expression vector containing a Zeocin resistance marker.

The mammalian expression vectors encoding the Glucagon-R or the GLP-1-R were transfected into Chinese hamster ovary (CHO) cells by the Attractene method. Stably expressing clones were obtained by Zeocin selection (250 μg/mL) upon limited dilution of cells resistant to the selection pressure. Glucagon-R and GLP-1-R cell clones expressing were picked, propagated and tested in the Glucagon-R and GLP-1-R efficacy assays as described below. One Glucagon-R expressing clone and one GLP-1-R expressing clone were chosen for compound profiling.

CHO cells expressing the human Glucagon-R, or human GLP-1-R were seeded 24 hours prior to the assay at 30,000 cells per well in 96-well microtiter plates in culture in 100 μl growth medium. On the day of analysis, growth medium was removed and the cells were washed once with 200 μl of assay buffer (Krebs-Ringer-buffer—KRBH). The buffer was removed and the cells were incubated for 15 min at room temperature in 10 μl KRBH (KRBH+10 mM HEPES, 5 mM NaHCO3, 0.1% (V/V) BSA) with 0.1 mM IBMX in deionized water containing increasing concentrations of test peptides. The reaction was stopped by the addition of lysis buffer (0.1% w/v BSA, 5 mM HEPES, 0.3% v/v Tween-20). After cell lysis for 10 min at room temperature, lysates were transferred to 384-well plates and 10 μl of acceptor/donorbead mixture as contained in the AlphaScreen™ cAMP Functional Assay Kit was added. After one hour of incubation at room temperature in the dark, the cAMP content was determined applying the AlphaScreen™ cAMP Functional Assay Kit from Perkin-Elmer according to manufacturer instructions. $EC_{50}$ and relative efficacies compared to reference compounds (glucagon and GLP-1) were calculated applying computer aided curve fitting. The GLP-1/glucagon ratio is calculated as defined earlier. See Tables 1A and 1B.

TABLE 1A

| Compound | EC50 hGCGR CHO-K1 [nM] | EC50 hGLP-1R CHO-K1 [nM] | Ratio GLP-1/ Glucagon |
|---|---|---|---|
| 1 | 0.90 | 0.54 | 0.60 |
| 2 | 0.31 | 0.77 | 2.48 |
| 3 | 0.35 | 0.91 | 2.60 |
| 4 | 1.56 | 0.38 | 0.24 |
| 5 | 0.46 | 0.16 | 0.35 |
| 6 | 0.46 | 0.35 | 0.76 |
| 7 | 0.45 | 0.27 | 0.60 |
| 8 | 0.29 | 0.41 | 1.41 |
| 9 | 0.25 | 0.35 | 1.40 |
| 10 | 0.23 | 0.23 | 1.00 |
| 11 | 0.61 | 0.64 | 1.05 |
| 12 | 0.43 | 0.37 | 0.86 |
| 13 | 0.98 | 0.51 | 0.52 |
| 14 | 0.54 | 0.53 | 0.98 |
| 15 | 0.61 | 0.19 | 0.31 |
| 16 | 1.58 | 0.20 | 0.13 |

TABLE 1B

| Compound | EC50 hGCGR CHO-K1 [nM] | EC50 hGLP-1R CHO-K1 [nM] | Ratio GLP-1/ Glucagon |
|---|---|---|---|
| 17 | 0.05 nM | 0.23 nM | 4.6 |
| 18 | 0.14 nM | 0.87 nM | 6.2 |
| 19 | 0.08 nM | 0.27 nM | 3.38 |
| 20 | 0.68 nM | 0.23 nM | 0.34 |
| 21 | 1.32 nM | 0.12 nM | 0.09 |
| 22 | 0.10 nM | 0.24 nM | 2.40 |
| 23 | 0.25 nM | 0.13 nM | 0.52 |
| 24 | 0.92 nM | 0.11 nM | 0.12 |
| 25 | 0.16 nM | 0.31 nM | 1.94 |

The two sets of compounds were tested in experiments performed using the same protocol in different laboratories.

Example 4

Agonistic Activity on Endogenous GLP-1 Receptor

Agonistic activity of the test compounds on endogenous GLP-1 receptors was determined using a murine insulinoma cell line. Intracellular cAMP was used an indicator of receptor activation.

Cells were cultured for 24 h at a density of 10,000 cells/well in a 384-well plate. Medium was removed and 10 µL KRBH buffer (NaCl 130 mM, KCl 3.6 mM, $NaH_2PO_4$ 0.5 mM, $MgSO_4$ 0.5 mM, $CaCl_2$ 1.5 mM) containing test compound or GLP-1 (at increasing concentrations from 0.1 pM to 100 nM) or solvent control (0.1% (v/v) DMSO) was added to the wells for 15 minutes at a temperature of 26° C.

The cellular cAMP content is measured using the AlphaScreen cAMP Functional Assay Kit (Perkin Elmer). Measurement was performed using the Envision (PerkinElmer) according to manufacturer's recommendations.

All measurements were performed in quadruplicate.

Results were converted into cAMP concentrations using a cAMP standard curve prepared in KRBH buffer containing 0.1% (v/v) DMSO. The resulting cAMP curves were plotted as absolute cAMP concentrations (nM) over log (test compound concentration) and analyzed using the curve fitting program XLfit.

Parameters calculated to describe the both the potency as well as the agonistic activity of each test compound on the endogenous GLP-1 receptors were:

pEC50 (negative logarithmic value of EC50, a concentration resulting in a half-maximal elevation of cAMP levels, reflecting the potency of the test compound);

Percent control (% CTL)(% cAMP elevation for each test compound concentration normalized based on the GLP-1-induced maximum cAMP response (100% CTL)). See Table 2.

TABLE 2

| Compound | EC50 GLP-1R (murine insulinoma cells) [nM] |
|---|---|
| 1 | 1.47 |
| 2 | 1.41 |
| 3 | 1.06 |
| 4 | 0.95 |
| 5 | 0.54 |
| 6 | 1.14 |
| 7 | 0.84 |
| 8 | 0.95 |
| 9 | 1.02 |
| 10 | 0.33 |
| 11 | 1.01 |
| 12 | 1.62 |
| 13 | 1.06 |
| 14 | 0.72 |
| 15 | 0.30 |
| 16 | 0.33 |
| 17 | 0.89 |
| 18 | 0.99 |
| 19 | 0.33 |
| 20 | 0.27 |
| 21 | 0.30 |
| 22 | 0.35 |
| 23 | 0.31 |
| 24 | 0.33 |
| 25 | 0.41 |

Example 5

Agonistic Activity on Endogenous Glucagon Receptor

Agonistic activity of the test compounds on endogenous glucagon receptor was determined by measuring their effect on rate of glycogen synthesis in primary rat hepatocytes. Upon activation of the glucagon receptor, an inhibition of the glycogen synthesis rate is expected. Rate of glycogen synthesis was determined by counting the amount of radioactively labeled glucose incorporated into the cellular glycogen stores in a defined period of time.

Primary rat hepatocytes were cultured at a density of 40,000 cells/well in a 24-well plate for 24 hours at 37° C. and 5% $CO_2$.

Medium was discarded and the cells washed with PBS. 180 µL of KRBH-based buffer containing 0.1% BSA and glucose at a concentration of 22.5 mM was then added to the wells, followed by test compound and 40 µCi/ml D-[U14C] glucose (20 µL each). Incubation was continued for 3 hours.

At the end of the incubation period, the incubation buffer was aspirated and cells washed once with ice-cold PBS before lysis by incubation for 30 min at room temperature with 100 µL 1 mol/l NaOH.

Cell lysates were transferred to 96-well filter plates and glycogen precipitated by incubating the filter-plates for 120 min at 4° C. followed by washing the filter plates 4 times with ice-cold ethanol (70%). The resulting precipitates were filtered to dryness and the amount of incorporated $^{14}$C-glucose determined by using a Topcount scintillation counter according to manufacturer's recommendations.

Wells with vehicle controls (0.1% (v/v) DMSO in KRBH buffer) were included as reference for non-inhibited glycogen synthesis (100% CTL). Wells without added D-[U$^{14}$C] glucose were included as controls for non-specific background signal (subtracted from all values). Endogenous glucagon peptide was used as a positive control.

All treatments were performed at least in triplicates.

Parameters calculated to describe the both the potency as well as the agonistic activity of each test compound on the endogenous glucagon receptor are pEC50 and % CTL.

% CTL is determined by calculating the percentage of CPM/well in the presence of the test compound compared to the CPM/well of the vehicle control after subtracting the background CPM/well:

[CPM/well(basal)−CPM/well(sample)]*100/[CPM/well(basal)−CPM/well(control)]

An activator of the glucagon receptor will result in an inhibition of the glycogen synthesis rate and will give % CTL values between 0% CTL (complete inhibition) and 100% CTL (no observable inhibition).

The resulting activity curves were plotted as absolute counts (unit: cpm/sample) over log (test compound concentration) and analyzed using the curve fitting program XLfit.

pEC50 (negative logarithmic value of EC50) reflects the potency of the test compound.

TABLE 3

| Compound | EC50 GLP-1R Rat hepat. [nM] |
|---|---|
| 1 | 0.13 |
| 1 | 0.02 |
| 2 | 0.43 |
| 3 | 0.16 |
| 4 | 0.35 |
| 5 | 0.03 |
| 6 | 2.87 |
| 7 | 1.92 |
| 8 | 1.10 |
| 9 | 0.37 |
| 10 | 0.04 |
| 12 | 0.24 |
| 13 | 0.67 |
| 14 | 0.10 |
| 15 | 0.17 |

TABLE 3-continued

| Compound | EC50 GLP-1R Rat hepat. [nM] |
|---|---|
| 16 | 1.85 |
| 17 | 0.18 |
| 18 | 0.18 |
| 19 | 0.06 |
| 20 | 0.39 |
| 21 | 3.40 |
| 22 | 0.28 |
| 23 | 1.32 |
| 24 | 6.15 |
| 25 | 0.15 |

The terms $EC_{50}$ and $pEC_{50}$ quoted in relation to GLP-1R activation could equally be regarded as $IC_{50}$ and $pIC_{50}$ in relation to glycogen synthesis.

Example 6

Estimate of Pharmacokinetic Parameters

Pharmacokinetic parameters of the test compounds were determined after subcutaneous and intravenous administration to C57Bl/6J mice.

8 week old male C57Bl/6J mice were obtained from Taconic (Denmark) weighing approximately 20-25 g at time of arrival at the test facility. The mice were caged in European standard cages type III with light cycle of 12-hour dark and 12-hour light (lights on 06.00). Both diet, Altromin 1324 (Altromin, Germany), and water was administered ad libitum during the whole experimental period. The 8-11 week animals were imported to the laboratory at least 7 days before the start up of the experimental procedure in order to assure proper acclimatization. After sampling the mice were euthanized by cervical dislocation.

The compounds were first dissolved in 0.096% aqueous ammonia to a nominal concentration of 2 mg/ml, and then diluted to the desired dosing strength (4 µM) in sterile PBS containing 25 mM phosphate buffer, pH 7.4. Subcutaneous and intravenous injections corresponding to 20 nmol/kg were given. The GLP-1-glucagon dual agonists were administered for subcutaneous dosing in the neck region and via a lateral tail vein for intravenous dosing.

Blood samples (250 µl) were collected from the periorbital plexus at time points 0.5, 2, 4, 6, 12, 16, 20, 24 h for subcutaneous and 10, 30 min, 3, 6, 12, 18, 24 h for intravenous administration into ice-chilled K$_3$EDTA tubes and centrifuged for 5 minutes at 4° C. within 20 minutes of sampling. Plasma (>100 µl) was separated to ice-chilled Micronic tubes, immediately frozen, and kept at −70° C. until analysed for plasma concentration for the respective GLP-1-glucagon compound using LC-MS/MS. Individual plasma concentration-time profiles were analysed by a non-compartmental approach in WinNonLin v6.3 (Pharsight inc, Mountain View, Calif., USA), and the resulting pharmacokinetic parameters determined. See Table 4.

TABLE 4

| | SC | | | | IV | |
|---|---|---|---|---|---|---|
| Compound | Mean Residence Time (hr) | Bioavailability (%) | Tmax (hr) | Terminal half life (hr) | Clearance (L/hr/kg) | Terminal half life (hr) |
| 1 | 12.6 | 52 | 4 | 6.2 | 0.0102 | 5.2 |
| 2 | 11.2 | 59 | 4 | 5.1 | 0.0111 | 5.0 |
| 3 | 9.8 | 52 | 6 | 3.9 | 0.0115 | 4.1 |

TABLE 4-continued

| Compound | SC | | | | IV | |
|---|---|---|---|---|---|---|
| | Mean Residence Time (hr) | Bioavailability (%) | Tmax (hr) | Terminal half life (hr) | Clearance (L/hr/kg) | Terminal half life (hr) |
| 4 | 12.5 | 53 | 4 | 6.4 | 0.0111 | 7.4 |
| 5 | 7.6 | 81 | 4 | 3.8 | 0.0111 | 4.0 |
| 6 | 10.6 | 47 | 4 | 4.3 | 0.0094 | 3.7 |
| 7 | 12.8 | 75 | 4 | 8.6 | 0.0132 | 5.5 |
| 8 | 8.1 | 42 | 4 | 4.1 | 0.0077 | 3.9 |
| 9 | 4.7 | 34 | 2 | 2.9 | 0.0383 | 0.9 |
| 10 | 6.5 | 80 | 2 | 3.7 | 0.0213 | 3.0 |
| 11 | 12.5 | 64 | 4 | 5.0 | 0.0094 | 3.9 |
| 12 | 8.3 | 43 | 6 | 4.3 | 0.0135 | 4.1 |
| 13 | 14.7 | 76 | 4 | 8.6 | 0.0089 | 6.3 |
| 14 | 12.2 | 64 | 4 | 6.1 | 0.0135 | 6.2 |
| 15 | 17.4 | 97 | 6 | 10.5 | 0.0077 | 6.0 |
| 16 | 7.5 | 80 | 2 | 5.0 | 0.0187 | 4.8 |

Example 7

Oral Glucose Tolerance Test (OGTT) in C57BL/6J Mice

Male C57BL/6J mice were fasted for 10 h before they received an oral glucose bolus of 2 g/kg body weight. Peptides were dissolved in saline buffered with 25 mM phosphate and administered at a dose of 10 nmol/kg body weight by subcutaneous injection 4 h before the glucose bolus. Control animals received a vehicle injection only. Group size was 7 animals per group. A pre-dose and a pre-glucose (0 min) blood sample were obtained by tail bleeding and blood glucose was measured with a glucometer. Additional samples of tail blood for measuring blood glucose were obtained 15 min, 30 min, 60 min, 90 min and 120 min after the glucose challenge. Glucose excursion was quantified by calculating the total area under the blood glucose-time curve (AUC) between 0 min and 120 min. Calculation of AUC was done by the trapezoidal rule without baseline correction. The data are presented as mean±S.E.M. Statistical comparisons were conducted by one-way ANOVA followed by Tukey's post test. Vehicle alone was used as a control. See Table 5.

TABLE 5

| Compound | AUC (% Ctrl) |
|---|---|
| 1 | 66 |
| 2 | 66 |
| 3 | 70 |
| 4 | 65 |
| 5 | 46 |
| 6 | 50 |
| 7 | 57 |
| 8 | 50 |
| 9 | 57 |
| 10 | 46 |
| 11 | 61 |
| 12 | 56 |
| 13 | 55 |
| 14 | 59 |
| 15 | 42 |
| 16 | 44 |

Example 8

Sub-Chronic Effects of Glucagon-GLP-1 Receptor Dual Acting Agonists on Adiposity in Diet-Induced Obese C57BL/6J Mice Male C57BL/6J mice (Taconic A/S, Denmark) at an age of 5 weeks were maintained on a 12:12 hour light-dark cycle on a high-fat diet (60% of total energy from fat, D12492, Research Diet Inc.) for 20 weeks. All mice (housed 2 per cage) were then mock-treated for a week to acclimatize the animals to handling and injections. Subsequently, the mice were stratified according to body fat mass (measured by magnetic resonance technique) and body weight into 9 groups (n=9-12). Animals were thereafter treated twice daily with subcutaneous injections (5 ml/kg) of vehicle (25 mM phosphate buffer, pH 7.4) or test substances (5 nmol/kg per administration, in equivalent amount of vehicle) for a total of 31 days. The daily injections were given at the start and at the end of the light phase. Body weight, food and water intake were determined daily throughout the study. The data are presented in Table 6 as mean body weight change±S.E.M. S.E.M. is defined as standard error of the mean and was calculated using the formula: S.E.M.=SD/square root (n), where SD is the standard deviation and n the number of observations (in this case animals/group).

Statistical analyses were performed using Graph Pad Prism version 5. The measured parameters were compared using one-way ANOVA followed by Dunnett's multiple comparison test. Differences were considered statistically significant at $p<0.05$.

TABLE 6

| Treatment Group | Mean body weight change (%) | SEM | Significance of difference vs. vehicle group |
|---|---|---|---|
| Vehicle | 4.8 | 1.3 | |
| Liraglutide | −2.3 | 1.5 | ** |
| Compound 2 | −5.1 | 1.9 | *** |
| Compound 7 | −8.7 | 1.5 | *** |
| Compound 14 | −9.5 | 1.1 | *** |
| Compound 15 | −10.9 | 1.6 | *** |
| Compound 16 | −12.2 | 1.1 | *** |

** $p < 0.01$,
*** $p < 0.001$ vs vehicle

The invention claimed is:

1. A compound having the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide which has the formula:
HSQGTFTSDYSKYLDS-K(Hexadecanoyl-isoGlu)-AAEDFVEWLLRA (SEQ ID NO:7),
and Z is absent or is a sequence of 1-20 amino acid units independently selected from the group consisting of Ala, Leu, Ser, Thr, Tyr, Cys, Glu, Lys, Arg, Dbu, Dpr and Orn,
or a pharmaceutically acceptable salt thereof.

2. A compound according to claim 1 having the formula:
HSQGTFTSDYSKYLDS-K(Hexadecanoyl-isoGlu)-AAEDFVEWLLRA (SEQ ID NO:7),
or a pharmaceutically acceptable salt thereof.

3. A composition comprising a compound according to claim 1 or 2 in admixture with a carrier.

4. A composition according to claim 3, wherein the composition is a pharmaceutical composition, and the carrier is a pharmaceutically acceptable carrier.

5. A method of inhibiting weight gain or promoting weight loss in an individual in need thereof comprising administering a compound according to claim 1 or 2.

6. A method of lowering circulating LDL levels, and/or increasing HDL/LDL ratio in an individual in need thereof comprising administering a compound according to claim 1 or 2.

7. A method of treating or reducing obesity, morbid obesity, morbid obesity prior to surgery, obesity linked inflammation, obesity linked gallbladder disease, obesity induced sleep apnea, diabetes, metabolic syndrome, hypertension, atherogenic dyslipidimia, atherosclerois, arteriosclerosis, coronary heart disease, peripheral artery disease, stroke or microvascular disease comprising administering a compound according to claim 1 or 2 to a patient in need thereof.

8. The method of claims 5 to 7, wherein the compound is administered as part of a combination therapy together with an agent for treatment of diabetes, obesity, dyslipidemia or hypertension.

9. The method of claim 8, wherein the agent for treatment of diabetes is a biguanide, a sulfonylurea, a meglitinide, a glinide, a DPP-IV inhibitor, a glitazone, a GLP-1 agonist, an insulin or an insulin analogue.

10. The method of claim 8, wherein the agent for treatment of obesity is a glucagon-like peptide receptor 1 agonist, peptide YY receptor agonist or analogue thereof, cannabinoid receptor 1 antagonist, lipase inhibitor, melanocortin receptor 4 agonist, or melanin concentrating hormone receptor 1 antagonist.

11. The method of claim 8, wherein the agent for treatment of hypertension is an angiotensin-converting enzyme inhibitor, angiotensin II receptor blocker, diuretic, beta-blocker, or calcium channel blocker.

12. The method of claim 8, wherein the agent for treatment of dyslipidaemia is a statin, a fibrate, a niacin or a cholesterol absorbtion inhibitor.

13. A therapeutic kit comprising a compound according to claim 1 or 2 or a composition according to claim 3 or 4.

14. The compound H-HSQGTFTSDYSKYLDS-K(Hexadecanoyl-isoGlu)-AAEDFVEWLLRA-$NH_2$ (Compound 7) (SEQ ID NO:7), or a pharmaceutically acceptable salt thereof.

15. The method of claim 9, wherein the biguanide is metformin.

* * * * *